United States Patent
Kennedy

(10) Patent No.: US 9,233,119 B2
(45) Date of Patent: Jan. 12, 2016

(54) USE OF HGMA-TARGETED PHOSPHOROTHIOATE DNA APTAMERS TO SUPPRESS CARCINOGENIC ACTIVITY AND INCREASE SENSITIVITY TO CHEMOTHERAPY AGENTS IN HUMAN CANCER CELLS

(71) Applicant: MIAMI UNIVERSITY, Oxford, OH (US)

(72) Inventor: Michael A. Kennedy, Oxford, OH (US)

( * ) Notice: Subject to any disclaimer, the term of this patent is extended or adjusted under 35 U.S.C. 154(b) by 8 days.

(21) Appl. No.: 14/037,554

(22) Filed: Sep. 26, 2013

(65) Prior Publication Data

US 2014/0107188 A1   Apr. 17, 2014

Related U.S. Application Data

(60) Provisional application No. 61/706,228, filed on Sep. 27, 2012.

(51) Int. Cl.
| | |
|---|---|
| C07H 21/02 | (2006.01) |
| C07H 21/04 | (2006.01) |
| A61K 31/70 | (2006.01) |
| A61K 31/7068 | (2006.01) |
| C12N 15/115 | (2010.01) |
| A61K 31/7088 | (2006.01) |
| A61K 31/7125 | (2006.01) |
| A61K 31/713 | (2006.01) |
| C12Q 1/68 | (2006.01) |

(52) U.S. Cl.
CPC .......... *A61K 31/7068* (2013.01); *A61K 31/7088* (2013.01); *A61K 31/713* (2013.01); *A61K 31/7125* (2013.01); *C12N 15/115* (2013.01); *C12N 2310/16* (2013.01); *C12N 2310/315* (2013.01)

(58) Field of Classification Search
None
See application file for complete search history.

(56) References Cited

U.S. PATENT DOCUMENTS

| | | | | |
|---|---|---|---|---|
| 6,080,588 | A * | 6/2000 | Glick | 436/508 |
| 8,497,250 | B2 * | 7/2013 | Vater et al. | 514/44 R |
| 2009/0192100 | A1 * | 7/2009 | Vater et al. | 514/44 |
| 2010/0323354 | A1 * | 12/2010 | Bullerdiek | 435/6 |

OTHER PUBLICATIONS

Cui et al Biochemistry vol. 46:13059-13066, 2007.*
Watanabe et al Cancer Letters, vol. 315:18-27, 2012.*
NIH Public Access, Author Manuscript; Adv Drug Deliv. Rev. Author manuscript; available to PMC Apr. 30, 2011; 62(6): 592-605. doi: 10.1016/j.addr.2010.03.003; Moleuclar Diagnostic and Drug Delivery Agents based on Aptamer-Nanometerial Conjugates.
Nanotechnology and aptamers: application in drug delivery; available online Jun. 19, 2008; 8 pages.
Targeted nanoparticle-aptamer bioconjugates for cancer chemotherapy in vivo; PNAS, Apr. 18, 2006; vol. 103, No. 16, pp. 6315-6320.

* cited by examiner

*Primary Examiner* — Sean McGarry
(74) *Attorney, Agent, or Firm* — Renner Kenner Greive Bobak Taylor & Weber

(57) ABSTRACT

Elevated high mobility group A (HMGA) protein expression in human cancer cells, and especially human pancreatic cancer cells, is correlated with resistance to the chemotherapy agent gemcitabine. The present invention uses HMGA-targeted AT-rich phosphorothioate DNA (AT-sDNA) aptamers to suppress HMGA carcinogenic activity. Cell growth of human pancreatic cancer cells (AsPC-1 and Miapaca-2) transfected with AT-sDNA were monitored after treatment with gemcitabine. Significant increases in cell death in AT-sDNA transfected cells compared to non AT-rich sDNA treated cells were observed in both cell lines. The data indicates the potential use of HMGA targeted DNA aptamers to enhance chemotherapy efficacy in human cancer treatment, and in particular human pancreatic cancer treatment.

9 Claims, 13 Drawing Sheets

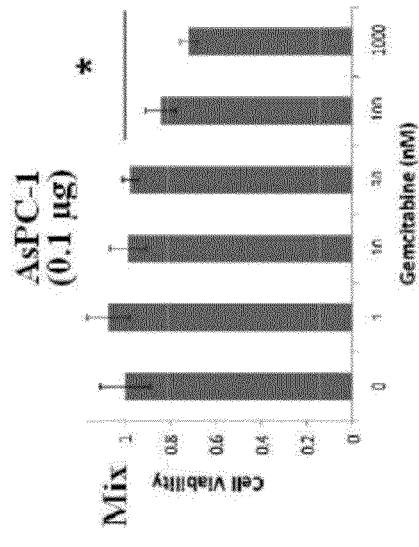
FIG. 11A
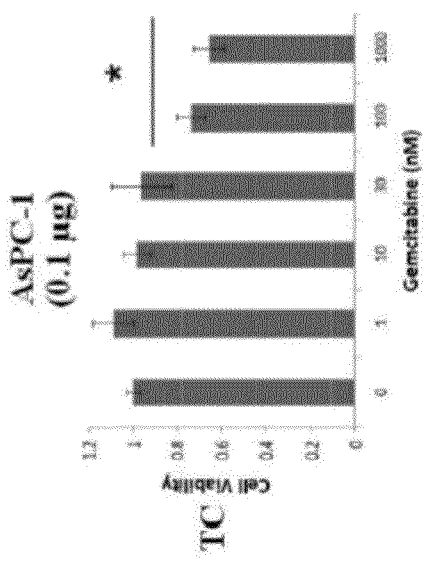
FIG. 11B
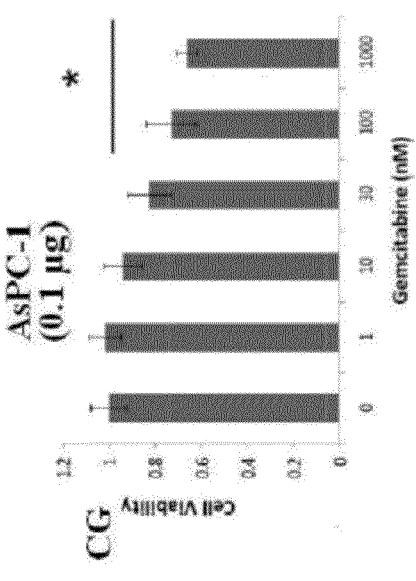
FIG. 11C
FIG. 11D

USE OF HGMA-TARGETED PHOSPHOROTHIOATE DNA APTAMERS TO SUPPRESS CARCINOGENIC ACTIVITY AND INCREASE SENSITIVITY TO CHEMOTHERAPY AGENTS IN HUMAN CANCER CELLS

CROSS REFERENCE TO RELATED APPLICATIONS

This application claims the benefit of U.S. provisional patent application Ser. No. 61/706,228 entitled "Use of HGMA-targeted phosphorothioate DNA aptamers to suppress carcinogenic activity and increase sensitivity to gemcitabine chemotherapy in human pancreatic cancer cells," filed Sep. 27, 2012, and incorporated herein by reference in its entirety.

REFERENCE TO GOVERNMENT SUPPORT

The invention was developed at least in part with the support of NIH grant number 1R15CA152985. The government may have certain rights in the invention.

FIELD OF THE INVENTION

The present invention relates to the use of HMGA-targeted AT-rich phosphorothioate DNA (AT-sDNA) aptamers to suppress HMGA carcinogenic activity in human cancer cells and to increase the effectiveness of chemotherapy agents.

BACKGROUND OF THE INVENTION

Elevated levels of high-mobility group A (HMGA) protein expression have been reported in almost every type of human cancer, including colorectal cancer, pancreatic cancer, and breast cancer. There are two forms of HMGA proteins, HMGA1 and HMGA2, which are encoded from two different genes. Both forms of HMGA are non-histone chromatin architectural transcription factors found broadly in eukaryotes. HMGA proteins are expressed at high levels in embryonic tissues during early development and at very low levels in normal differentiated somatic adult cells. Regulation of gene expression is a primary function of HMGA in these cells and HMGA proteins are involved in both positive and negative regulation of genes responsible for apoptosis, cell proliferation, immune response and DNA repair. Overexpression of HMGA has been shown to increase cell proliferation contributing to tumor growth.

In addition, it has been shown that HMGA1 interacts with the p53 tumor suppressor protein and inhibits its apoptotic activity. It has also been shown that high expression levels of HMGA1 are responsible for chemotherapy resistance in pancreatic cancer cell lines and that suppression of HMGA1 expression by siRNA restored the cells sensitivity to gemcitabine. HMGA2 is responsible for maintaining Ras-induced epithelial-mesenchymal transition that promotes tissue invasion and metastasis. Down regulation of overexpressed HMGA2 has been shown to inhibit cell proliferation in human pancreatic cancer cell lines. While the precise role that HMGA plays in cancer is not yet completely understood, HMGA has been suggested as a potential biomarker for tumor progression and is a drug target for cancer therapy development.

An early structural study showed that HMGA does not adopt a conventional protein structure composed of α helices or β sheets but rather binds in the minor groove of AT-rich double-stranded DNA through crescent-shaped DNA binding motifs referred to as "AT-hooks." In contrast to classical transcription factors that bind specific DNA sequences, HMGA acts as an architectural transcription factor that binds a specific type of DNA structure, i.e. the minor groove of A:T tract DNA. Due to this unique DNA binding property of HMGA, several cancer therapy drugs, such as FR900482 and FL317, have been designed as competitive HMGA1 inhibitors that bind to the minor groove of AT-rich DNA. These drugs however, have shown high toxicity in humans. Recently, it has been shown that Spiegelmer NOX-A50 is a potent inhibitor of HMGA1 activity and proposed the use of artificial HMGA1 substrates that block HMGA1 binding to its natural DNA substrate. In principle, decreasing all HMGA protein activity could result in inhibition of unwanted cell proliferation and reestablishment of apoptosis, reducing cancer progression.

Nucleic acid ligands designed or selected to inhibit the activity of pathogenic proteins are referred to as aptamers or "decoys". Nucleic acid aptamers contain variable sequences and/or modified chemical structures to facilitate binding to their protein targets with high specificity and an equal to, or higher, affinity compared to their unmodified oligomer counterparts. They are widely studied for biotechnological and therapeutic applications because they have little or no immunogenicity compared to antibodies and several applications have been reported. For example, one study has shown that overexpression of a 60-nucleotide RNA decoy used as a antiviral treatment showed inhibition of Tat-mediated HIV replication in vitro by 90%. In another study, a 2'-fluoropyrimidine RNA was designed as a vascular endothelial growth factor inhibitor that reduced lung metastasis in mice. A DNA aptamer targeting transcription factor E2F, which is essential in cellular proliferation regulation, was shown to decrease cell proliferation in vascular smooth muscle cells.

In addition to engineered specificity, an important property of DNA aptamers is that they are sometimes designed to be resistant to endogenous nuclease activity in vivo. For example, both phosphorothioate DNA (sDNA), which contains sulfur substituted for one oxygen atom in the phosphodiester backbone, and phosphorodithioate DNA, which contains sulfur substitution of two oxygen atoms in the phosphodiester backbone, have been shown to have shown increased resistance to nuclease S1 and Deoxyribonuclease I (DNase I) activity as the number of sulfur substitutions increases.

Since down regulation of both HMGA1 and HMGA2 proteins contributes to the inhibition of tumor growth, the strategy of targeting both HMGA1 and HMGA2 may result in a potentially more potent therapeutic strategy than targeted inhibition of either protein alone. Therefore, there is a need for nuclease resistant DNA aptamers that both inhibit pancreatic cancer tumor growth and increase the sensitivity of pancreatic cancer cells to chemotherapy by down regulation of both HMGA1 and HMGA2 proteins and are resistant to endogenous nuclease attack.

SUMMARY OF THE INVENTION

The present invention is generally directed phosphorothioate substituted DNA aptamers (sDNA aptamer(s)) active against HMGA proteins that contain multiple HMGA AT-hook binding sites (AT-sDNA) to compete for HMGA protein binding to genomic DNA and directly inhibit HMGA activity in cancer cells. Since both HMGA1 and HMGA2 bind AT-rich DNA, the sDNA aptamer is intended to inhibit the activity of both forms of HMGA. The sDNA aptamer may be transfected into human cancer cells including, in some embodiments, pancreatic adenocarcinoma cells.

In some embodiments, the present invention may be a sDNA aptamer for suppressing the activity of HMGA proteins in human cancer cells. In some embodiments, the sDNA aptamer of the present invention suppresses the activity of HMGA proteins in human pancreatic cancer cells.

In some embodiments, the sDNA Aptamer may have a length of from about 7 to about 30 base pairs and a nucleotide sequence comprising from about 5 to about 18 adenine or thymine nucleotides. In some embodiments, the length of the sDNA aptamer is from about 17 to about 30 base pairs. In some embodiments, the length of the sDNA aptamer is from about 20 to about 30 base pairs. In some embodiments, the length of the sDNA aptamer is from about 17 to about 30 base pairs. In some embodiments, nucleotide sequence comprises a sequence of from about 15 to about 18 adenine or thymine nucleotides. In some embodiments, the sDNA aptamer has a sequence of 18 adenine or thymine nucleotides. In some embodiments, the segment of adenine or thymine nucleotides in said nucleotide sequence is consecutive. In some embodiments, the segment of adenine or thymine nucleotides in said nucleotide sequence is alternating or randomly mixed. In some embodiments, the segment of adenine or thymine nucleotides in said nucleotide sequence may consist of a total of three segments of 5-6 consecutive adenine or thymine or mixed adenine and thymine residues with each segment spaced by 1-3 guanine or cytosine residues. In some embodiments, the sDNA aptamer may have the sequence 5'-G*G*G*A*A*A*A*A*A*T*T*T*T-*T*T*A*A*A*A*A*A*C*C*C-3' (SEQ ID NO: 1) wherein the "*" are phosphorothioate linkages. In some embodiments, the aptamer sequence is self-complementary. In some embodiments, the aptamer sequence is not self-complementary, requiring that two distinct sequences must be synthesized and annealed.

In some embodiments, the sDNA aptamer may inhibit HMGA protein activity in human pancreatic adenocarcinoma cells and may increase sensitivity of human pancreatic adenocarcinoma cells to gemcitabine, which is used in the treatment of various human cancers including non-small cell lung cancer, pancreatic cancer, bladder cancer and breast cancer. The sDNA aptamer may also rescue cellular apoptosis induced by gemcitabine treatment and may prevent excess HMGA from binding to chromosomal DNA transcription factors and other proteins involved in regulating apoptosis and cell proliferation in tumor progression.

In some embodiments, the sDNA aptamer may have substantial resistance to the activity of endogenous nucleases, such as Deoxyribonuclease I.

One method of practicing the claimed invention may include a method increasing sensitivity to chemotherapy agents in human cancer cells comprising: (i) administering a therapeutically effective amount of a chemotherapy agent to a patient; and (ii) administering a therapeutically effective amount of a sDNA aptamer having a length of from about 7 to about 30 base pairs and a nucleotide sequence comprising from about 5 to about 18 adenine or thymine nucleotides to the patient whereby the sensitivity of the human cancer cells to the chemotherapy agent is increased. In some embodiments, the human cancer cells are human pancreatic cancer cells. In some embodiments, the chemotherapy agent is gemcitabine.

Another method for practicing the invention may include a method of suppressing the activity of High Mobility Group A (HMGA) proteins in human cancer cells comprising: (i) administering a therapeutically effective amount of a chemotherapy agent to a patient; and (ii) administering a therapeutically significant amount of the sDNA aptamer having a length of from about 7 to about 30 base pairs and a nucleotide sequence comprising from about 5 to about 18 adenine or thymine nucleotides to the patient whereby the activity of High Mobility Group A (HMGA) proteins in the human cancer cells is reduced. In some embodiments, the human cancer cells are human pancreatic cancer cells. In some embodiments, the chemotherapy agent is gemcitabine.

Yet another method for practicing the invention may include a method for treating human pancreatic adenocarcinoma comprising: (i) administering a therapeutically effective amount of gemcitabine, or a pharmaceutically acceptable salt thereof, to a patient; and (ii) administering a therapeutically significant amount of the phosphorothioate substituted sDNA aptamer having a length of from about 7 to about 30 base pairs and a nucleotide sequence comprising from about 5 to about 18 adenine or thymine nucleotides to the patient whereby the number of the pancreatic adenocarcinoma cells in the patient is reduced. In some embodiments, the pancreatic adenocarcinoma cells in the patient are reduced in an amount greater than the reduction of the number of the pancreatic adenocarcinoma cells achieved through administration of said gemcitabine, or a pharmaceutically acceptable salt thereof, to said patient without administering the phosphorothioate substituted sDNA aptamer.

BRIEF DESCRIPTION OF THE DRAWINGS

For a more complete understanding of the features and advantages of the present invention, reference is now made to the detailed description of the invention along with the accompanying figures in which.

Triplicates of each sample were run on the gel and analyzed with the Alpha Imager. The relative HMGA1 densities were obtained by dividing HMGA1density by TBP density. The values were analyzed pair wise using a student t-test, with p values <0.05 considered a significant change (*p<0.05). TATA binding protein (TBP) was used as a loading control.

Figure 6A:
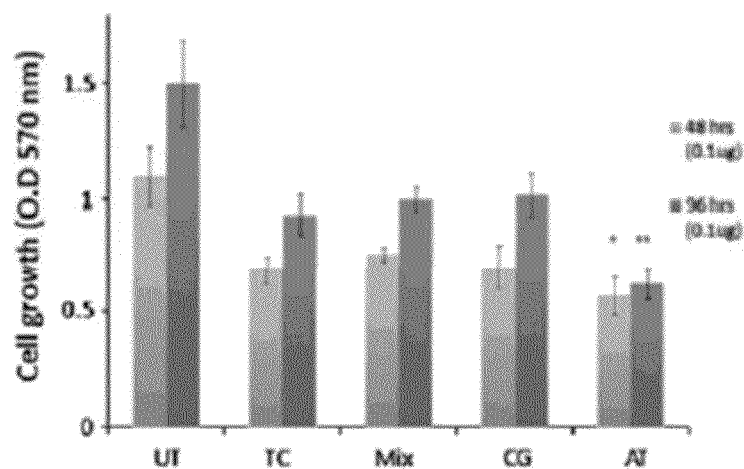
Figure 6B:
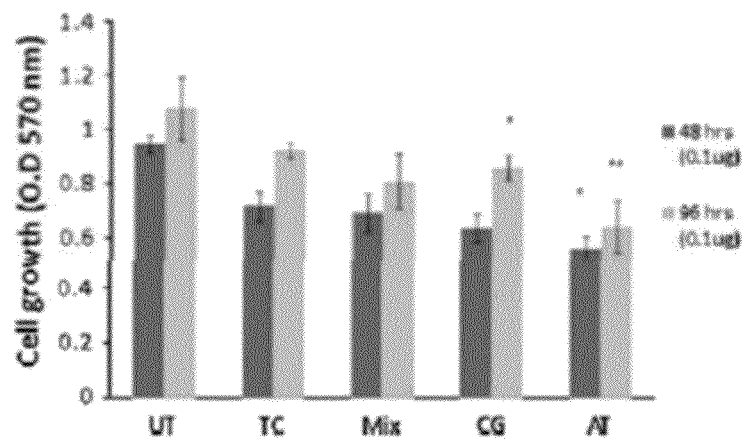

FIGS. 6A and 6B reports the results of a cell viability assay done after sDNA transfection. Miapaca-2 (FIG. 6A) and AsPC-1 (FIG. 6B) cells were transfected with two doses of sDNA. Cells were fixed 48 and 96 hours after transfection and analyzed with the crystal violet assay as described in the methods. The absorbance was measured at 570 nm in quadruplicate. All data from control cells were combined and averaged. The values were analyzed pair wise with TC using a student t-test, with p values <0.05 considered a significant change (*p<0.05, **p<0.01).

Figure 8A:
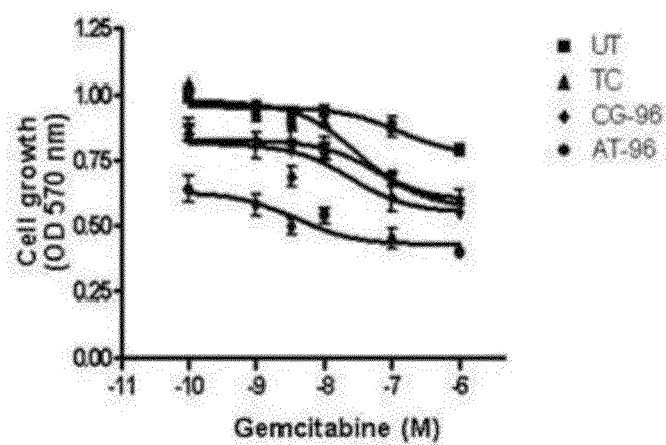
Figure 8B:
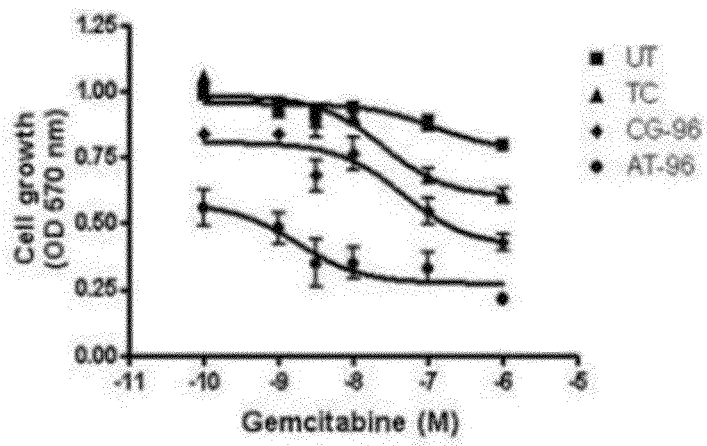
Figure 8C:
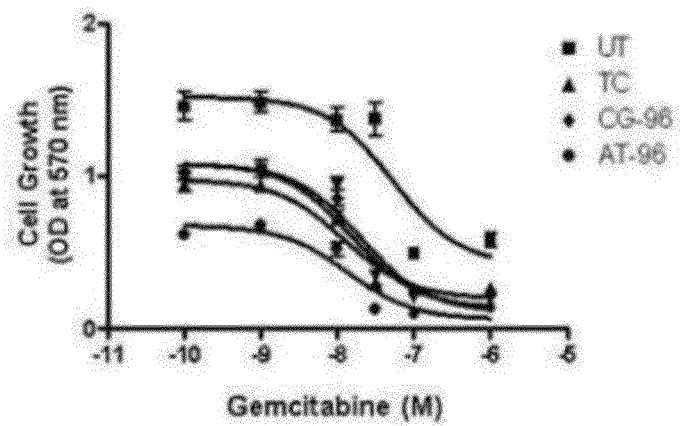
Figure 8D:
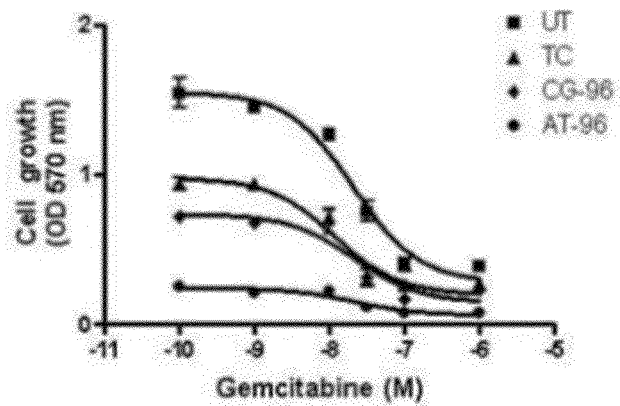

FIGS. 8A-8D are a series of graphs reporting $IC_{50}$ determinations for various doses of sDNA transfection with gemcitabine treatment for AsPC-1: 0.1 µg transfection (FIG. 8A) and 0.25 µg transfection (FIG. 8B), and for Miapaca-2: 0.1 µg transfection (FIG. 8C) and 0.25 µg transfection (FIG. 8D).

Figure 10A:
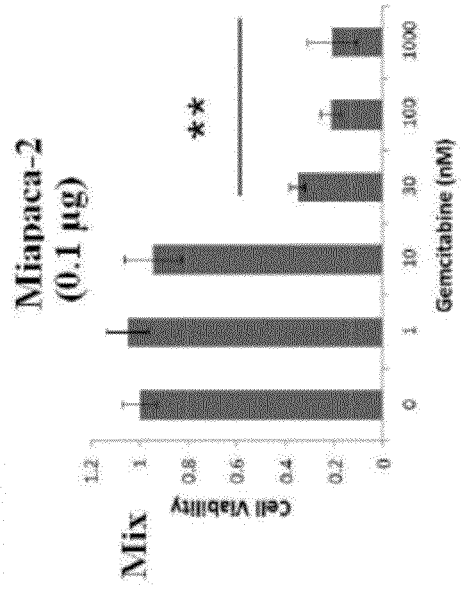
Figure 10B:
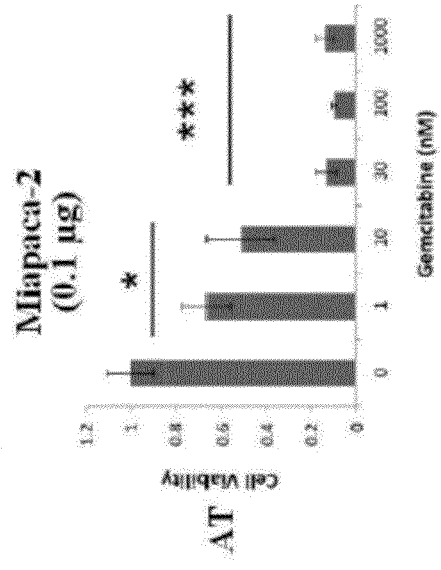
Figure 10C:
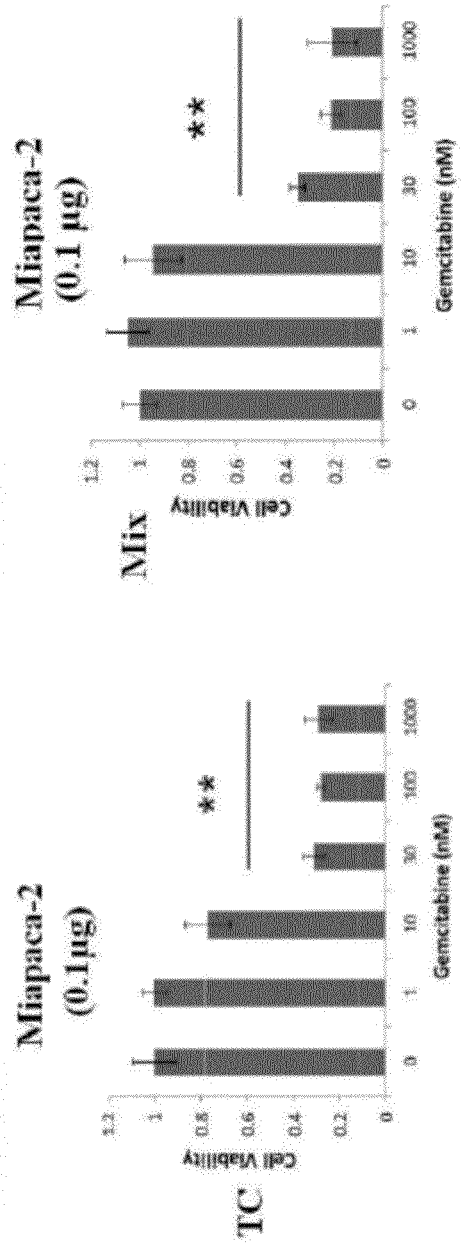
Figure 10D:
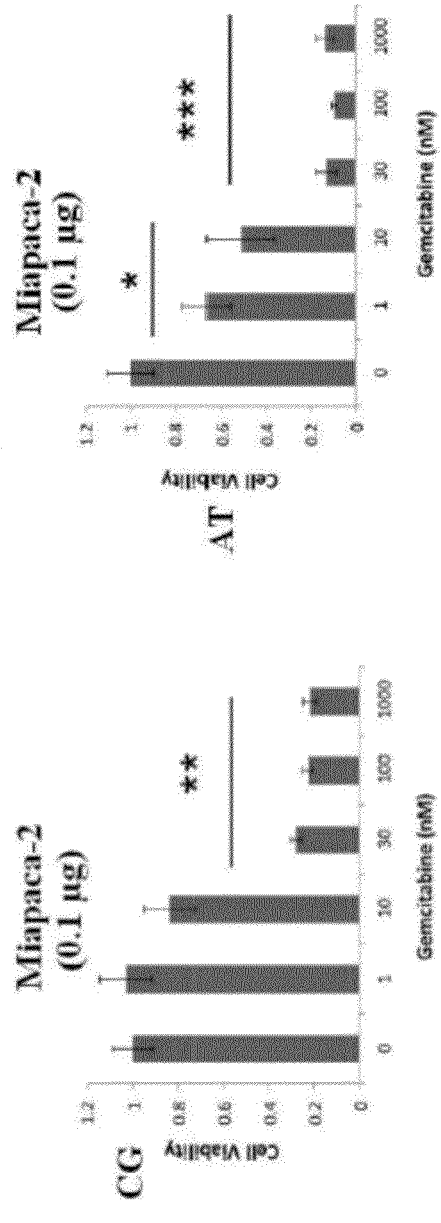
Figure 12A:
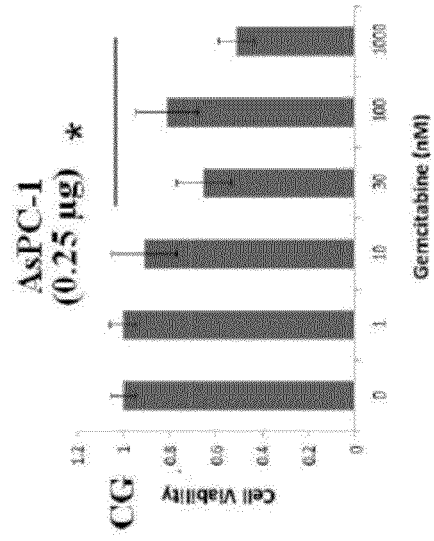
Figure 12B:
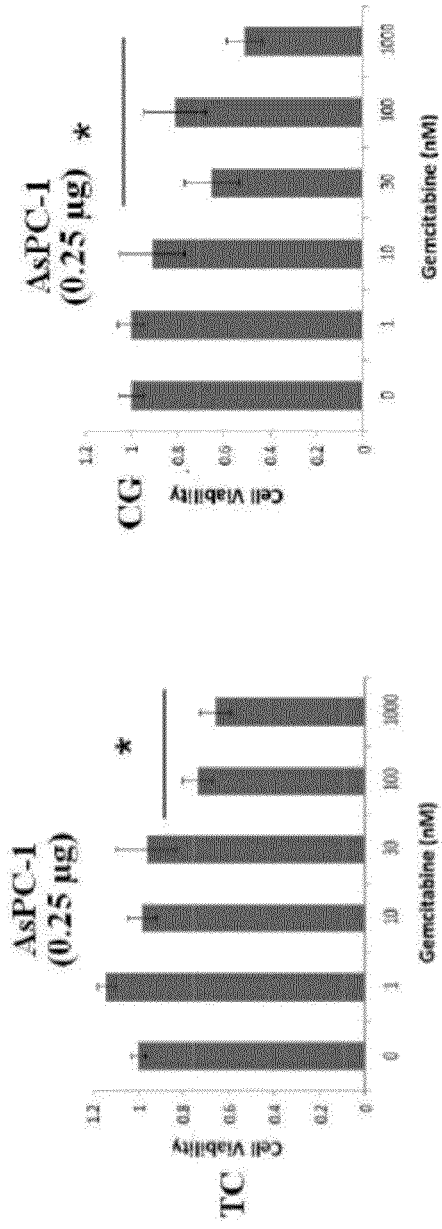
Figure 12C:
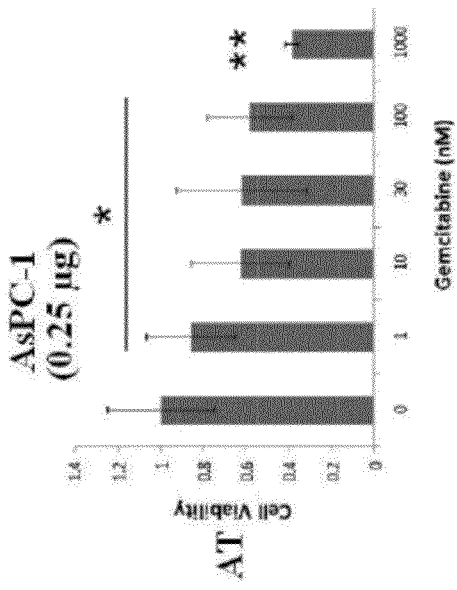

FIGS. 10A-D, 11A-D, and 12A-C are a series of graphs reporting a dose dependent response to gemcitabine treatment after sDNA transfection at 96 hours. FIG. 10 is a series of graphs reporting a dose dependent response to gemcitabine treatment after sDNA transfection in Miapaca-2 at 96 hours. The Miapaca-2 cells were transfected with 0.1 µg of TC-sDNA (FIG. 10A), Mix-sDNA (FIG. 10A), CG-sDNA (FIG. 10C), and AT-sDNA (FIG. 10D). FIGS. 11A-D and 12A-C are graphs reporting dose dependent responses to gemcitabine treatment in AsPC-1 cells at 96 hours at 0.1 µg (FIGS. 11A-D) and 0.25 µg (FIGS. 11A-D) transfection per $5 \times 10^4$-$1 \times 10^5$ cancer cells. The AsPC-1 cells were transfected with 0.1 µg of TC-sDNA (FIG. 11A), Mix-sDNA (FIG. 11A), CG-sDNA (FIG. 11C), and AT-sDNA (FIG. 11D) and with 0.25 µg of TC-sDNA (FIG. 12A), CG-sDNA (FIG. 12B), and AT-sDNA (FIG. 12C). The data was normalized with the 0 nM gemcitabine treated cells and the resulting value defined as a value of 1. The values were analyzed in pairs using a student t-test, with p values <0.05 considered a significant change (*p<0.05, p<0.01, *p<0.001).

Figure 7A:
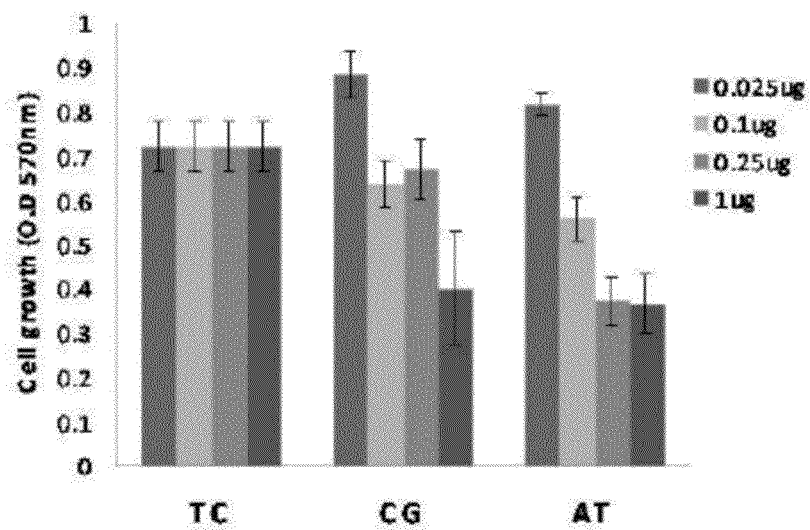
Figure 7B:
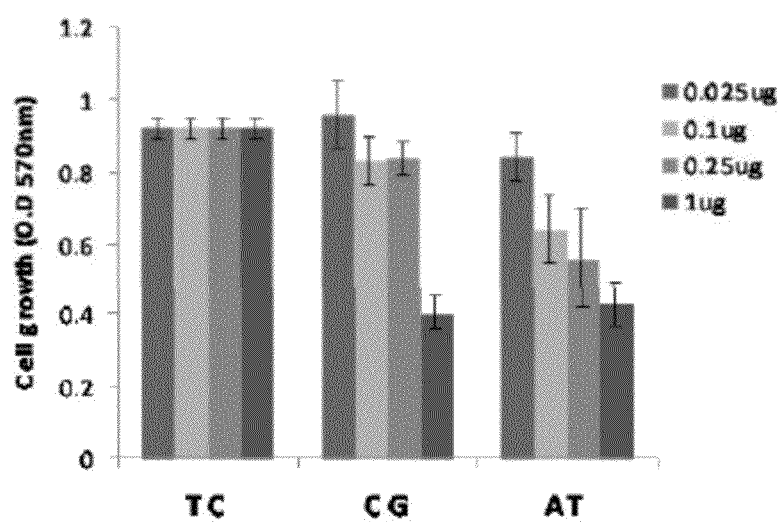

FIGS. 7A and 7B are graphs showing dose dependant response to sDNA transfection in AsPC-1 at 48 (FIG. 7A) and 96 hours (FIG. 7B). Cells were transfected with 0.025 µg, 0.1 µg, 0.25 µg, and 1.0 µg, of CG-sDNA, and AT-sDNA. Data was normalized with the 0 nM gemcitabine treated cells defined as a value of 1. The values were analyzed pair wise using a student t-test, with p values <0.05 considered a significant change (*p<0.05).

Figure 9A:
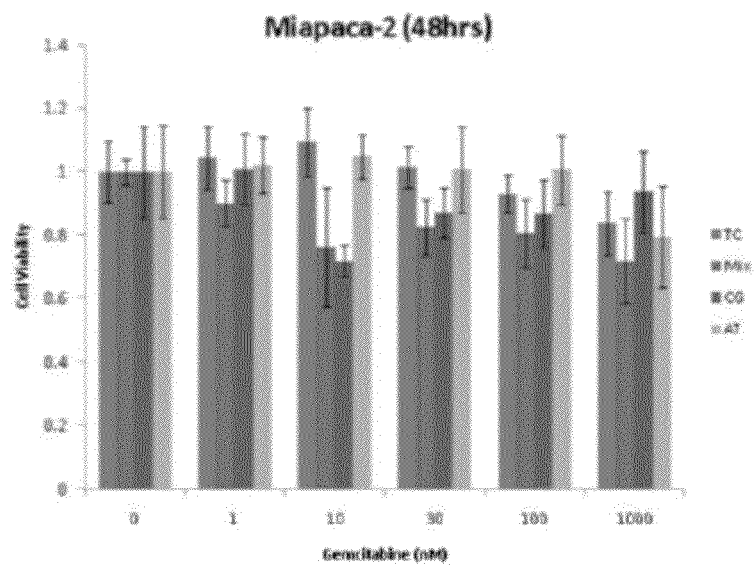
Figure 9B:
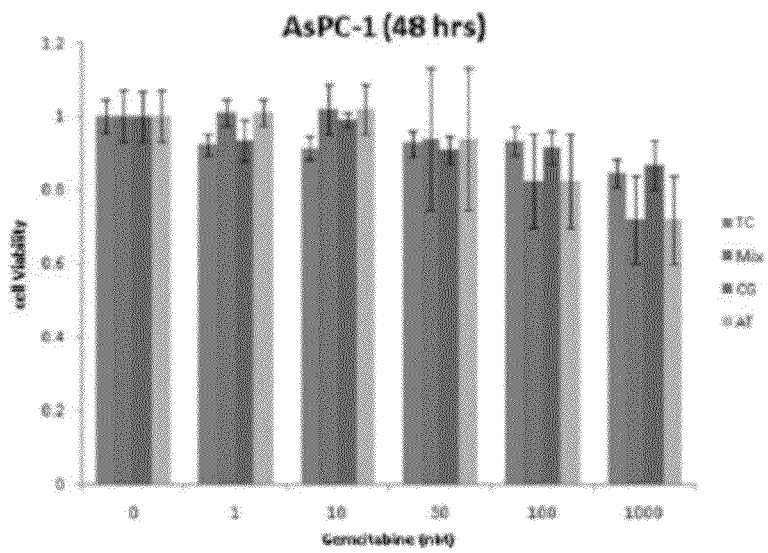

FIGS. 9A and 9B are graphs showing dose dependant response to gemcitabine treatment after sDNA transfection in Miapaca-2 (FIG. 9A) and AspC-1 (FIG. 9B) at 48 hours. Cells were transfected with 0.1 ug of Mix-sDNA. Data was normalized with the 0 nM gemcitabine treated cells defined as a value of 1. The values were analyzed pair wise using a student t-test, with p values <0.05 considered a significant change (*p<0.05).

DETAILED DESCRIPTION OF ILLUSTRATIVE EMBODIMENTS

While the making and using of various embodiments of the present invention are discussed below, it should be appreciated that the present invention provides many applicable inventive concepts that can be embodied in a variety of specific contexts. The specific embodiments discussed herein are merely illustrative of specific ways to make and use the invention and do not delimit the scope of the invention.

The abbreviations used herein should be well understood by those of ordinary skill in the art, but are set forth here for clarity. Accordingly, as used herein, "ATfDNA" means fluorescence labeled DNA; "AT-sDNA" means AT-rich phosphorothioate DNA; "CG-sDNA" means CG-rich phosphorothioate DNA; "DMEM" means Dulbecco's Modified Eagle Medium; "DNase I" means Deoxyribonuclease I; "EMSA" means electrophoretic mobility shift assay; "FBS" means fetal bovine serum; "HMGA" means high mobility group A; "$IC_{50}$" means half maximal inhibitory concentration; "IPTG" means isopropyl β-D-1-thiogalactopyranoside; "Mix-sDNA" means random sequence phosphorothioate DNA; "sDNA" means phosphorothioate DNA; "TAE" means Tris base, acetic acid and EDTA buffer; "cDNA" means complementary DNA; "PVDF" means polyvinlidene fluoride; "PBST" means phosphate buffered saline with Tween 20; "BSA" means bovine serum albumin; "RPIM" means Roswell Park Memorial Institute medium; "SDS-PAGE" means sodium dodecyl sulfate polyacrylamide gel electrophoresis; and "TPB" means TATA binding protein.

Unless otherwise specified, compounds referenced herein are "commercially available" and may be obtained from standard commercial sources including, without limitation, Acros Organics (Pittsburgh Pa.), Aldrich Chemical (Milwaukee Wis., including Sigma Chemical and Fluka), Apin Chemicals Ltd. (Milton Park U.K.), Avocado Research (Lancashire U.K.), SDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire U.K.), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.), Novabiochem and Argonaut Technology.

As set forth above, elevated levels of high-mobility group A (HMGA) protein expression have been reported in almost every type of human cancer. Overexpression of HMGA has been shown to increase cell proliferation contributing to tumor growth and HMGA1 interacts with the p53 tumor suppressor protein and inhibits its apoptotic activity. It has also been shown that high expression levels of HMGA1 are responsible for chemotherapy resistance in pancreatic cancer cell lines and that suppression of HMGA1 expression by siRNA restored the cells sensitivity to chemotherapy agents like gemcitabine. HMGA2 is responsible for maintaining Ras-induced epithelial-mesenchymal transition that promotes tissue invasion and metastasis. Down regulation of overexpressed HMGA2 has been shown to inhibit cell proliferation in human pancreatic cancer cell lines.

Broadly speaking, the present invention is directed to use of high mobility group A (HMGA)-targeted AT-rich phosphorothioate DNA (AT-sDNA) aptamers as essentially a "decoy" to bind with and limit the activity of HMGA proteins, particularly in cancer cells. HMGA proteins contain multiple AT-hook binding sites, and will bind with certain areas of the AT-sDNA aptamers of the present invention rather than with genomic DNA or other receptors, as it would but for the presence of the AT-sDNA aptamers, In this way, the AT-sDNA aptamers of the present invention directly inhibit HMGA protein activity in cancer and other cells where the HMGA proteins are being overexpressed. Since both HMGA1 and HMGA2 bind AT-rich DNA, the disclosed sDNA aptamer is intended to inhibit the activity of both forms of HMGA, which may result in potentially more potent therapeutic strategies than inhibiting the activity of either protein alone. HGMA-targeted phosphorothiate DNA aptamers increase sensitivity to gemcitabine chemotherapy in human pancreatic cancer cell lines. See also, Watanabe et al. Cancer Letters 315 (2012) 18-27, the disclosure of which is hereby incorporated by reference in its entirety.

The AT-sDNA aptamers of the present invention are an adenine and thymine rich phosphorothiate substituted oligonucleotide sequence of from about 7 to about 30 nucleotides in length. In some embodiments, the AT-sDNA aptamer may be from about 15 to about 30 nucleotides in length. In some embodiments, the AT-sDNA aptamer may be from about 20 to about 30 nucleotides in length.

Each HGMA protein is believed to have three AT-hook binding sites and the AT-sDNA aptamers of the present invention may bind to one, two or all three of the sites, depending upon the affinity of the particular AT-sDNA aptamer for the protein. See Watanabe et al., Characterization of the Stoichiometry of HMGA1/DNA Complexes, The Open Biochemistry Journal, 2013, 7, 73-81, the disclosure of which is incorporated herein by reference in its entirety. It is believed that each one of these AT-hook binding sites is configured to receive a segment of AT-sDNA aptamer having a sequence of 5 or 6 adenine or thymine nucleotides. As will be appreciated, AT-sDNA aptamers having the highest affinity for the HMGA proteins will have three sequences of 5 or 6 adenine or thymine nucleotides for each AT-hook binding site on the HGMA protein, for a total of from 15 to 18 AT basepairs. In some embodiments, the AT-sDNA aptamer may have 10-12 AT basepairs. In some embodiments, the AT-sDNA aptamer has 18 AT basepairs. In some embodiments, the AT-sDNA aptamer has 18 AT basepairs. While it is not necessary to practice the invention, it is preferable if the AT basepairs which bind to each of the AT-hook binding site on the HGMA protein are consecutive.

It should also be appreciated that the sequence or sequences of the AT-sDNA aptamers which bind to each of the AT-hook binding site on the HGMA protein can be comprised entirely of adenine, entirely of thymine, or of a mixture of the two. In one embodiment of the present invention, the AT-sDNA aptamer has the nucleotide sequence, 5'-G*G*G*A*A*A*A*A*A*T*T*T*T*T*T*T*A*A*A*A*A*A*C*C*C-3' (SEQ ID NO: 1) where each "*" is a phosphorothioate linkage. In some embodiments, the AT-sDNA aptamer may be a 21 base oligonucleotide having the nucleotide sequence 5'-C*C*C*A*A*A*A*A*A*A*A*A*A*A*A*A*A*A*C*C*C-3' (SEQ ID NO: 2) where each "*" is a phosphorothioate linkage. In some embodiments, the AT-sDNA aptamer may be a 21 base oligonucleotide having the nucleotide sequence 5'-G*G*G*T*T*T*T*T*T*T*T*T*T*T*T*T*T*T*G*G*G-3' (SEQ ID NO: 3) where each "*" is a phosphorothioate linkage. In some embodiments, the AT-sDNA aptamer may be a 21 base oligonucleotide having the nucleotide sequence composed of any mixture of A and T nucleotides where the linkage between each nucleotide is a phosphorothioate linkage.

The AT-sDNA aptamers of the present invention should have a long half life against endogenous nuclease activity and to that end the aptamers of the present invention are made from sDNA and have phosphorothiate linkages between all of their nucleotides. It has been found that HGMA will bind sDNA with a similar affinity compared to normal DNA. It has also been found that the presence of non AT-rich DNA did not interfere with HMGA binding to AT-rich DNA.

AT-sDNA aptamers consistent with various embodiments of the present invention may be synthesized by any method known in the art. Suitable aptamers may be custom synthesized by a variety of commercial vendors, including by way of example, Integrated DNA Technologies of Coralville, Iowa (USA).

Further, while the AT-sDNA aptamers of the present invention has been discussed in terms of a single strand so that the invention may be more easily understood, it should be appreciated that the AT-sDNA aptamers of the present invention are double stranded and have a sulfur substitution in every linkage.

As one of ordinary skill in the art will appreciate, the single stranded AT-sDNA aptamer discussed above must be annealed with a complementary oligonucleotide strand to form the biologically active double-stranded AT-sDNA aptamers of the present invention. In some embodiments, the aptamer nucleotide sequence is self-complementary and only requires annealing to form the duplex form. In some embodiments, the aptamer sequence is not self-complementary, and in this case two distinct complementary sequences must be annealed to form the active duplex form of the aptamer. The complementary oligonucleotide strands may be synthesized by any method known in the art and are commercially available from a variety of vendors, including Integrated DNA Technologies of Coralville, Iowa (USA). In one embodiment, the oligonucleotide strands are annealed by combining stoichiometric amounts of each strand in a standard buffer and raising the temperature above the calculated melting temperature of the oligomers and letting the temperature slowly decrease to room temperature. After annealing, the AT-sDNA aptamer may be purified using gel filtration. In one embodiment the AT-sDNA aptamer may be purified by application onto a hydrophobic Sep-Pack column with elution for desalting if necessary. In one embodiment of the invention, the AT-sDNA aptamer is purified with a Sephadex G-25 column (GE Healthcare) in H2O.

The AT-sDNA aptamer may then be transfected into a cell by any known means. In one embodiment of the invention the AT-sDNA may be transfected into human pancreatic adenocarcinoma cells using Lipofectamine 2000, which is commercially available from Invitrogen™ (Life Technologies Corporation, Carlsbad, Calif. (USA)) used according to the manufacturer's protocol.

In some embodiments of the present invention, the AT-sDNA aptamer may be transfected into human cells in vivo by means of nanoparticle-aptamer bioconjugates. Suitable nanoparticle-aptamer bioconjugates are known in the art and may be created by any known means, including those means identified in Farokhzad O C, Karp J M, Langer R. Nanoparticle-aptamer bioconjugates for cancer targeting. Expert Opin Drug Deliv. 2006; 3:311-324. [PubMed: 16640493]; Levy-Nissenbaum E, Radovic-Moreno A F, Wang A Z, Langer R, Farokhzad O C. Nanotechnology and aptamers: applications in drug delivery. Trends Biotechnol. 2008; 26:442-449. [PubMed: 18571753]; and Lee J H, Yigit M V, Mazumdar D, Lu Y. Molecular diagnostic and drug delivery agents based on aptamer-nanomaterial conjugates. Adv Drug Deliv. Rev. 2010; 62:592-605. [PubMed: 20338204], the disclosures of which are incorporated herein by reference in their entirety.

A representative preparation of bioconjugate nanoparticles for delivery may be adapted from the manuscript of Farokhzad et al and summarized as follows. Bioconjugate nanoparticles may be composed of controlled release polymer nanoparticles and aptamers prepared for targeted delivery to prostate cancer cells. Specifically, poly(lactic acid)-block-polyethylene glycol (PEG) copolymer with a terminal carboxylic acid functional group (PLA-PEG-COOH) was prepared. Fifty microliters of PLA-PEG-COOH nanoparticle or microparticle suspension (~10 μg/μL in DNase RNase-free water) was incubated with 200 μL of 400 mmol/L 1-(3-dimethylaminopropyl)-3-ethylcarbodimide hydrochloride (EDC) and 200 μL of 100 mmol/L N-hydroxysuccinimide (NHS) for 15 minutes at room temperature with gentle stirring. The resulting NHS-activated particles were covalently linked to 50 μL of 3'-NH2-modified A10 PSMA aptamer (1 μg/μL in DNase RNase-free water) or 3'-NH2 and 5'-FITC-modified A10 PSMA aptamer. The resulting aptamer-nanoparticle bioconjugates were washed, resuspended, and preserved in suspension form in DNase RNase-free water.

As discussed above, once the AT-sDNA aptamer is transfected into the cell, it inhibits the activity of both forms of HMGA by competitive sequestration of excess HMGA. This inhibition of HMGA1 activity has been associated with increased cell death or apoptosis even in the absence of chemotherapy treatment. FIGS. 6A and 6B show an analysis of the growth of AsPC-1 cells transfected with CG-sDNA and AT-sDNA analyzed after 96 h to examine the effect of sDNA transfection on cell viability. Four different amounts of sDNA, 0.025 μg, 0.1 μg, 0.25 μg and 1.0 μg per well, were used to transfect $1 \times 10^5$ cells in 24-well plates. When cells were transfected with 1.0 μg of sDNA, more than half of the cells were dead after 96 h for both AT-sDNA (57%, P<0.001) and CG-sDNA (60%, P<0.001). This result showed that 1.0 μg of sDNA transfection was highly toxic to the cells independent of DNA sequence. Therefore, lower dosages of sDNA were used to characterize sensitivity to DNA transfection. When 0.25 μg sDNA was used for transfection, significantly lower viabilities were observed for both sDNA transfected cells. However, cell death was greater in cells transfected with AT-sDNA (44%, P<0.005) compared to CG-sDNA (16%, P<0.01). As the amount of sDNA transfected was decreased to 0.1 μg, the difference in the cell death rates between CG-sDNA and AT-sDNA transfection became more pronounced. For CG-sDNA transfected cells, 12% (P<0.05) cell death was observed whereas 33% (P<0.001) cell death was observed for AT-sDNA transfected cells. Transfection with 0.025 μg of sDNA had very little affect on cell growth, with only a 15% (P<0.05) decrease in viability for AT-sDNA transfected cells was found whereas the reduction in CG-sDNA transfected cells was not statistically significant compared to non-transfected cells, 4% (P>0.05). Only 0.25 μg and 0.1 μg sDNA treatments showed statistically significant differences between AT-sDNA and CG-sDNA transfected cells, P=0.007 and P=0.004 respectively. These results indicated that inhibition of HMGA1 activity allowed for increased cell death or apoptosis, even in the absence of chemotherapy treatment.

Furthermore, elevated HMGA protein expression in pancreatic cancer cells has been correlated with resistance to the chemotherapy agent gemcitabine, which is commonly used in combating pancreatic cancer as well as non-small cell lung cancer, bladder cancer and breast cancer. Use of the AT-sDNA aptamer in conjunction with standard chemotherapy treatments using gemcitabine may restore gemcitabine sensitivity by preventing excess HMGA1 from binding to chromosomal DNA transcription factors and other proteins involved in regulating apoptosis and cell proliferation in tumor progression. The HMGA-targeted AT-sDNA aptamer's inhibition of HMGA may also result in the rescue of cellular apoptosis induced by the gemcitabine treatment. Since these HMGA-targeted sDNA aptamers have no direct effect on HMGA gene expression levels, do not bind directly to genomic DNA and should not stimulate immunogenic responses, HMGA-targeted AT-sDNA aptamer treatment, potentially in localized combination therapy with gemcitabine, may render cancer cells more sensitive to existing chemotherapy reagents and result in fewer side effects.

As discussed above, by virtue of their phosphorothioate linkages, AT-sDNA aptamers show significant the endogenous nuclease resistance. In some embodiment of the invention, the AT-sDNA aptamers show significant resistance to the endogenous commercially available nuclease Deoxyribonuclease I (Fermentas Life Sciences).

Another aspect of the invention is a method for suppressing the activity of High Mobility Group A (HMGA) proteins in human pancreatic cancer cells comprising: (1) administering a therapeutically effective amount of a chemotherapy agent to a patient; and (2) administering a therapeutically effective amount of the phosphorothioate substituted sDNA aptamer of the present invention to the patient. As used herein, a chemotherapy agent is any cytotoxic antineoplastic agent that selectively targets rapidly dividing cells such as cancer cells. Methods of administration and therapeutically effective dosages for chemotherapy agents are well known in the art and those of ordinary skill in the art will be able to determine a suitable method of administration and therapeutically effective dosage amount without undue experimentation. In some embodiments, the chemotherapy agent may be gemcitabine. In some embodiments, the human cancer cells may be in human pancreatic cancer cells. The sDNA aptamer may be administered to the patient using any method known in the art for that purpose. In some embodiments, the AT-sDNA aptamer may be transfected into human cells in vivo by means of nanoparticle-aptamer bioconjugates.

Another aspect of the present invention is a method for increasing sensitivity to gemcitabine chemotherapy in human pancreatic cancer cells comprising (1) administering a therapeutically effective amount of gemcitabine, or a pharmaceutically acceptable salt thereof, to a patient; and (2) administering a therapeutically effective amount of the phosphorothioate substituted sDNA aptamer of the present invention to the patient. In some embodiments, the AT-sDNA aptamer may be transfected into human cells in vivo by means of nanoparticle-aptamer bioconjugates.

Yet another aspect of the invention is a method for treating human pancreatic adenocarcinoma comprising (1) administering a therapeutically effective amount of gemcitabine, or a pharmaceutically acceptable salt thereof, to a patient; and (2) administering a therapeutically effective amount of the phosphorothioate substituted sDNA aptamer of the present invention to the patient. In some embodiments, the AT-sDNA aptamer may be transfected into human cells in vivo by means of nanoparticle-aptamer bioconjugates, as discussed above.

In light of the foregoing, it should be appreciated that the present invention significantly advances the art by providing a novel and improved pancreatic cancer therapy using an HGMA-targeted phosphorothioate DNA aptamer. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

The methods and compositions described herein utilize or are produced using laboratory techniques well known to skilled artisans and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999, and Ausubel, F. M., et al., ed., Current Protocols in Molecular Biology. For pharmaceutical compositions and methods of treatment disclosed herein, dosage forms and administration regimes can be determined using standard methods known to skilled artisans, for example as set forth in standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. Organic syntheses including synthesis of radiolabelled organic compounds can be performed using methods and principles well known to skilled artisans, such as those set forth in standard texts such as Hedrickson et al., Organic Chemistry 3rd edition, McGraw Hill, New York, 1970; Carruthers, W., and Coldham, I., Modern Methods of Organic Synthesis (4th Edition), Cambridge University Press, Cambridge, U.K., 2004; Curati, W. L., Imaging in Oncology, Cambridge University Press, Cambridge, U.K., 1998; Welch, M. J., and Redvanly, C. S., eds. Handbook of Radiopharmaceuticals: Radiochemistry and Applications, J. Wiley, New York, 2003.

Materials and Methods

The above compounds and others disclosed herein can be obtained, made and tested for activity using the following procedures.

Expression and Purification of HMGA1 Protein

The cDNA for full length HMGA1b was cloned into pET-30b and over-expressed in *Eschericia coli* (*E. Coli*) BL21 (DE3). *E. coli* expressing HMGA1b was cultured at 37° C. to an $OD_{600}$ measurement of 0.8 to 1.0 $OD_{600}$. Protein expression was induced by the addition of 1 mM IPTG and shaking at 37° C. for 4-6 hours. HMGA1 was purified by trichloroacetic acid precipitation as described in R. Reeves, HMGA proteins: isolation, biochemical modifications, and nucleosome interactions. Methods in enzymology 375 (2004) 297-322, the disclosure of which is incorporated herein by reference. Overexpressed HMGA1b was further purified with a Sephadex G-25 column in $H_2O$ and lyophilized using a standard freezedrying procedure. The samples were resolublized in a 25 mM Tris-HCl (pH 6.5), 50 mM NaCl buffer for analysis.

Electrophoretic Mobility Shift Assays (EMSA)

The following 28-mer oligonucleotides were purchased from Integrated DNA Technologies (Coralville, Iowa, USA): ATf10 5'-(56FAM)-CGCGGGGCCGCCGC-GAAAAAAAAAAAACCC-3' (SEQ ID NO: 4), and ATs10 5'-GGGT*T*T*T*T*T*T*T*T*T*CGCGGCGGCCCCGC G-3' (SEQ ID NO: 5) (the "*" indicates the location of phosphorothioate linkage). ATf10 contained a fluorescence tag to serve as a marker for later analysis. These oligonucleotide samples were resuspended and annealed with complementary strands in annealing solution (100 mM NaCl, 10 mM MgCl2 in H2O). AT10f was annealed with its complementary strand without a fluorescence tag, and ATs10 was annealed with a strand with no sulfur substitution. The complimentary strands for these oligonucleotides are commercially available and were purchased from Integrated DNA Technologies (Coralville, Iowa, USA).

CG10 5'-GGGCCCCCCCCCCCGCGGCGGC-CCCGCG-3' (SEQ ID NO: 6) and Mix10 5'-GGGCGT-GACTGAGCGCGGCGGCCCCGC G-3' (SEQ ID NO: 7) were used as negative controls to demonstrate that the presence of these DNA molecules did not affect HMGA binding to AT-rich DNA. The HMGA protein samples were prepared in 25 mM Tris-HCl (pH 6.5), 50 mM NaCl, and the concentrations determined based on UV 220 nm absorbance ($\epsilon$=38, 200 mol-1 cm-1). The HGMA protein was mixed with DNA according to the ratio indicated in FIG. 1 of J. R. Huth, C. A. Bewley, M. S, Nissen, J. N. Evans, R. Reeves, A. M. Gronenborn, G. M. Clore, The solution structure of an HMG-I(Y)-DNA complex defines a new architectural minor groove binding motif. Nature structural biology 4 (1997) 657-665, the disclosure of which is incorporated herein by reference in its entirety and incubated at 4° C. for 15 minutes prior to gel analysis. The protein-DNA complexes were resolved on a 7.5% polyacrylmide gel and run with TAE buffer at 20 mA for 2-3 hours at 4° C. The DNA was detected at 495 nm using the VersaDoc™ Imaging System Model 3000 from BIO-RAD Laboratories, Inc. of Hercules, Calif. (USA). The gels were further stained with coomassie blue and visualized by an AlphaImager (Alpha Innotech, San Leandro, Calif.).

Nuclease Resistance Assays

The following 21 base oligonucleotides, all containing a run of either 15 consecutive adenines or thymines, were purchased from Integrated DNA Technologies, Inc. (Coralville, Iowa, USA): A15 5'-CCCAAAAAAAAAAAAAAAACCC-3' (SEQ ID NO: 8), T15 5'-GGGTTTTTTTTTTTTTTTGGG-3' (SEQ ID NO: 9), As10 5'-CC*CA*AA*AA*AA* AA-*AA*AA*AA*CC*C-5' (SEQ ID NO: 10), Ts10 5'-G*GG*TT*TT*TT*TT*TT*TT*TT*TG*GG-3' (SEQ ID NO: 11), Ts20 5'-G*G*G*T*T*T*T*T*T* T*T*T*T*T*T*T*T*T*G*G*G-3' (SEQ ID NO: 3), and As20 5'-C*C*C*A*A*A*A*A*A*A*A*A*A*A*A* A*A*A*C*C*C-3' (SEQ ID NO: 2). The asterisks ("*") indicate positions of sulfur substitutions in the phosphate backbone of the nucleotide chain and the number following the "s" in the name of the oligonucleotide sequence indicates the number of sulfur substitutions in each sequence. The samples were resuspended and annealed in an annealing solution in the following combinations: AT15 (A15 and T15), As10Ts10, As10Ts20 and As20Ts20.

Each of the AT15 (A15 and T15), As10Ts10, As10Ts20 and As20Ts20 combinations (0.25 nmol) was incubated with 0.5 unit of Deoxyribonuclease I (DNaseI) (Fermentas Life Sciences) at 37° C. up to 12 hours. As used herein, one unit of Deoxyribonuclease I is the amount necessary to completely degrade 1 µg of plasmid DNA in 10 min. at 37° C. The samples were resolved on a 7% polyacrylmide gel and run with TAE buffer at 401DA for 1-2 hours at 4° C. The gels were stained with ethidium bromide and visualized by an AlphaImager (Alpha Innotech, San Leandro, Calif.).

Cell Cultures

Human pancreatic adenocarcinoma cell lines, Panc-1, Miapaca-2 and AsPC-1, were obtained from the American Type Culture Collection (Manassas, Va.). Miapaca-2 and Panc-1 cells were grown in high glucose DMEM medium supplemented with 10% fetal bovine serum (FBS) purchased from Gibco-Life Technologies and 1% penicillin-streptomycin obtained from Sigma-Aldrich. Cells were maintained in 5% $CO_2$ humidified atmosphere at 37° C. AsPC-1 cells were grown in Roswell Park Memorial Institute medium supplemented with 10% FBS, and 1% penicillin-streptomycin. Cells were maintained in 5% $CO_2$ humidified atmosphere at 37° C. Confluent cells were trypsinized using trypsin-EDTA solution and seeded into 100 mm dishes and maintained. When cells were grown to 75-85% confluence in 100 mm culture dishes, the media was aspirated and cells were trypsinized. Fresh growth media containing 10% FBS was added to the trypsinized cells (10:1 ratio) and centrifuged for 5 minutes at 1,500 rpm at 4° C. After resuspending the cells in the appropriate medium, the cell count was measured using a "Neubauer Counting Chamber" hemocytometer obtained from Hauser Scientific through Fisher Scientific.

Cellular Protein Isolation and Western Blot Analysis

Cytoplasmic and nuclear protein extracts were prepared from pancreatic cancer cells using NE-PER extraction kit (Thermo Scientific, Rockford, Ill.). Protein concentrations were determined using a bicinchoninic acid assay with bovine serum albumin as a standard. Nuclear proteins that contained 25 or 15 µg total protein were separated by SDS-PAGE with a 4%-20% Criterion gradient gel (Bio-Rad Laboratories, Inc., Hercules, Calif.). The proteins were transferred to immuno-blot PVDF membrane (0.2 µm) (Bio-Rad Laboratories, Inc., Hercules, Calif.) and blocked in 5% dry milk in PBS supplemented with 0.2% Tween 20 (PBST). The PVDF membranes were then probed with 1:1000 dilution of rabbit anti-HMGA1 antibody (Santa Cruz Biotechnology Inc, Santa Cruz, Calif.) and 1:100 dilution of rabbit anti-HMGA2 antibody (Abcam plc, Cambridge, Mass.), in 3% BSA in PBST at 4° C. overnight. After three washes with PBST, the membrane was blotted with secondary antibody, ant-rabbit IgG-HRP (cell signaling) 1:5000 dilution in 1% dry milk in PBST at room temperature for 1 hour. An enhanced chemiluminescence detection (ECL, GE Healthcare Life Sciences, Piscataway, N.J.) system was used to detect target proteins. To ensure equal loading of the proteins between groups, membranes were re-probed with anti-TATA binding protein antibody (Abcam plc, Cambridge, Mass.).

sDNA Transfections

Cells were transfected with AT-rich phosphorothioate DNA (AT-sDNA): 5'-G*G*G*A*A*A*A*A*A*T*T*T*T*T*T*A*A*A*A*A*A*C*C*C-3' (SEQ ID NO: 1) (Integrated DNA Technologies), CG-rich phosphorothioate DNA (CG-sDNA): 5'-C*C*C*C*G*G*G*C*C*C* C*G*G*C*C* G*G*G*C*G*C*C*G*C-3' (SEQ ID NO: 12), and random phosphorothioate DNA (Mix-sDNA): 5'-C*C*C*A*C*T*G*C*A*G*T*C*G*G*A*C*T*C*A* C*T*C*G*C-3' (SEQ ID NO: 13), with the latter being used as a control that lacked a HMGA-specific binding sequence. These oligonucleotides are available from a variety of vendors through custom commercial synthesis. After annealing with complementary strands, the DNA was purified with a Sephadex G-25 column (GE Healthcare Life Sciences) in H2O. Both complementary strands also contained sulfur substitution at every position. Transfections using sDNA at concentrations of 0.1 and 0.25 µg per well were conducted with $5\times10^4$ and $1\times10^5$ Miapaca-2 and AsPC-1 cells, respectively, in 24-well plates and all data were collected in quadruplicate. Miapaca-2 and AsPC-1 cells were transfected with sDNA using Lipofectamine 2000 (Invitrogen,™ Life Technologies Corporation, Carlsbad, Calif.) according to the manufacturer's protocol.

Cell Growth Assays in the Presence of Gemcitabine Treatment

Cell growth was monitored using a modified crystal violet assay as previously described by S. Sheriff, M. Ali, A. Yahya, K. H. Haider, A. Balasubramaniam, H. Amlal, Neuropeptide Y Y5 receptor promotes cell growth through extracellular signal-regulated kinase signaling and cyclic AMP inhibition in a human breast cancer cell line. Molecular cancer research: MCR 8 (2010) 604-614., the disclosure of which is hereby incorporated by reference. Briefly, AsPC-1 cells grown in 10% FBS containing RPIM medium were trypsinized using a trypsin-EDTA solution commercially available from the Sigma-Aldrich, and used to seed fresh media in a 24-well plate with 105 cells per well.

Due to the shorter doubling time, 5,000 cells per well of Miapaca-2 cells were seeded in a 24-well plate in 10% FBS containing DMEM medium. After 48 hours, the cells were transfected with the selected sDNA using Lipofectamine 2000 (Invitrogen,™ Life Technologies Corporation, Carlsbad, Calif.) according to the manufacturer's protocol. The following day, media was changed to fresh media containing different concentrations of gemcitabine (0, 1, 10, 30, 100, 1000 nM). The cells were fixed 48 and 96 hours after gemcitabine treatment. The cells were then fixed with 4% paraformaldehyde in PBS for 20 minutes and stained in 0.1% crystal violet stain (Sigma-Aldrich) for 30 minutes. The cells were washed under running tap water, air dried, and extracted with 0.2% Triton™ X-100 for 30 minutes. Triton™ X-100 is a widely used non-ionic surfactant for recovery of membrane components under mild non-denaturing conditions and is commercial available from Sigma-Aldrich, among other vendors. The absorbance of the Triton X-100 was measured at 570 nm using a HTS microplate reader. All results were analyzed for statistical significance using a student's unpaired t-test. The half maximal inhibitory concentration ($IC_{50}$) values for gemcitabine treatment were determined using a Prism™ software program (Graphpad Software, San Diego, Calif.). A p-value of <0.05 was considered statistically significant.

Results

EXAMPLE 1

DNA Binding Assays

Figure 1A:
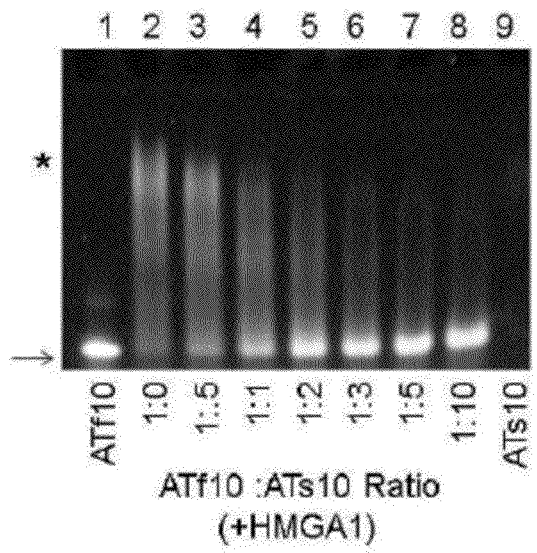
FIG. 1A is an image from an electrophoretic mobility shift assay (EMSA) of an HMGA1 competitive binding assay using sDNA and unmodified DNA. Lanes 1 and 9, ATf10 and ATs10 respectively, are controls that do not contain HMGA1. The ratios between HMGA1 and ATf10 were kept constant at 1.5 (excess HMGA1, lane 2) and an increased amount of ATs10 was added to the reactions in lanes 3 to 8.

In order to determine if HMGA1 DNA binding activity was affected by sulfur substitution in the DNA phosphodiester backbone, fluorescence labeled DNA (ATf10 DNA) was used in competitive binding assays against various sulfur substituted DNAs where different ratios of ATf10 DNA and ATs10 DNA were added to a constant amount of purified HMGA1 (FIG. 1A).

FIG. 1A shows an image from an electrophoretic mobility shift assay (EMSA) of an HMGA1 competitive binding assay using sDNA and unmodified DNA. Lanes 1 and 9 are controls, ATf10 and ATs10 respectively, that do not contain HMGA1. The ratios between HMGA1 and ATf10 were kept constant at 1.5 (excess HMGA1, lane 2) and an increased amount of ATs10 was added to the reactions in lanes 3 to 8.

The amount of free (unshifted) ATf10 DNA was determined by monitoring the absorbance intensity at 495 nm using a BIO-RAD VersaDoc Imaging System Model 3000 (Bio-Rad, Hercules, Calif.) A constant ratio of ATf10 DNA to HMGA1 of 1:1.5, resulted in nearly completely shifted ATf10 DNA in the absence of competitive sulfur-substituted DNA (FIG. 1A, lane2). As the ratio of ATs10 DNA to ATf10 DNA increased, the intensity of the free ATf10 DNA band increased (FIG. 1A, lanes 2-8), indicating that the ATs10 DNA was effectively competing for HMGA1 binding. Since ATs10 DNA has no fluorescence label, no signal could be detected when only ATs10DNA was added to HMGA1 (FIG. 1A, lane 9). At a 1:1 ratio of ATf10 DNA to ATs10 DNA, approximately half of the ATf10 DNA was detected in the unshifted position (FIG. 1A, lane 4) indicating that HMGA1 was able to bind ATs10 DNA with a similar affinity compared to normal DNA.

Thus, the following experiments were conducted under the assumption that HMGA1 bound sDNA with a similar affinity compared to normal DNA.

Figure 1B:
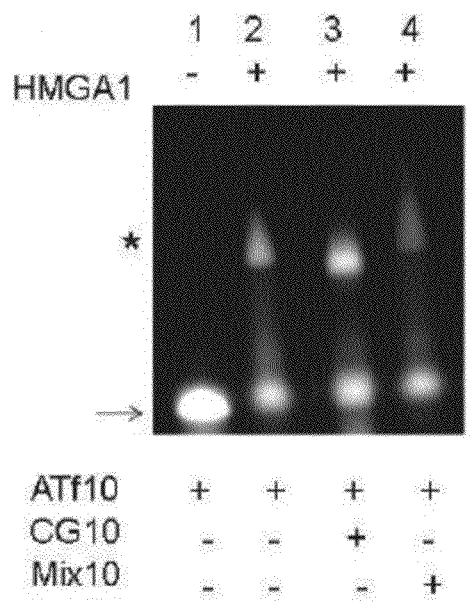
FIG. 1B is an image from an EMSA of HMGA1 competitive binding assay using CG10 and Mix10 DNA. Lanes 2-4 contain equal amounts of ATf10 and CG10 or Mix10. ATf10 DNA: HMGA1 in lanes 2-4 was kept constant at a 1:1 ratio. The arrow indicates free (unshifted) DNA and the * indicates the complex (shifted bands) with ATf10 DNA. The images were taken at 495 nm using a BIO-RAD VersaDoc Imaging System Model 3000 in order to visualize the ATf10.

In order to demonstrate preferential HMGA binding to AT-rich DNA compared to CG-rich or mixed sequence DNA lacking AT tracks, gel shift assays were conducted using two controls, CG10 and Mix10. The results of the gel shift assays are reported on FIG. 1B. FIG. 1B shows an image from the EMSA of HMGA1 competitive binding assay using CG10 and Mix10 DNA. Lanes 2-4 contain equal amounts of ATf10 and CG10 or Mix10. ATf10 DNA: HMGA1 in lanes 2-4 was kept constant at a 1:1 ratio. The arrow indicates free (unshifted) DNA and the "*" indicates the complex (shifted bands) with ATf10 DNA. The images were taken at 495 nm using a BIO-RAD VersaDoc Imaging System Model 3000 in order to visualize the ATf10.

The CG10 sequence only contained a mixture of C and G, and the Mix10 sequence contained a random sequence of A, T, C, G with no AT-stretch. The formation of an HMGA/ATf10 DNA complex (FIG. 1B, lane 2*) was still observed when CG10 or Mix10 DNA was present (FIG. 1B, lanes 3 and 4).

These results not only demonstrated the preference of HMGA for binding AT-rich DNA, but also demonstrated that the presence of non AT-rich DNA did not interfere with HMGA binding to AT-rich DNA.

EXAMPLE 2

Nuclease Resistance Assays

Figure 2:
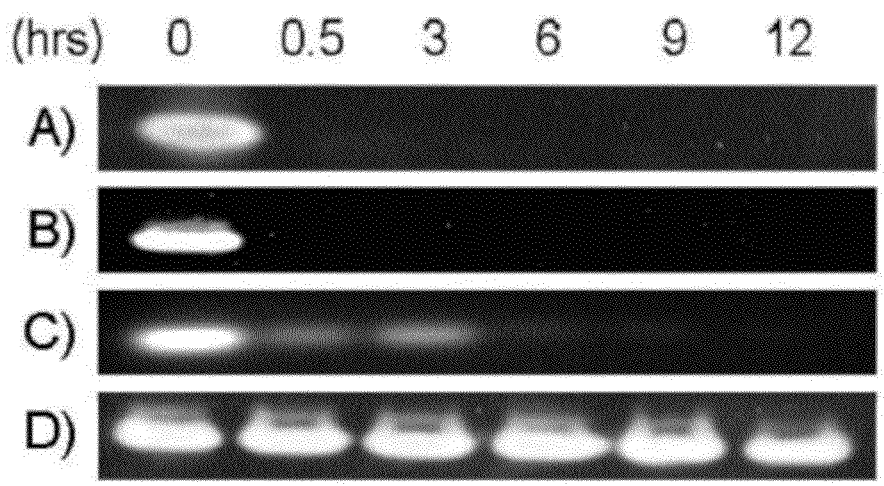
FIG. 2 is an image from a nuclease resistance assay for sDNA with DNase I. 0.25 nmol of A) AT15, B) As10Ts10, C) As10Ts20 and D) As20Ts20 were incubated for 0 to 12 hours and run on a 7% native polyacrylamide gel. The gel was stained with ethidium bromide and visualized using an AlphaImager.

In order to have any potential clinical value, DNA-based aptamers targeting HMGA1 must have a long half-life against endogenous nuclease activity. To explore how nuclease resistance was affected by sulfur substitution in the HMGA1 DNA aptamers, sDNAs containing different numbers and positions of sulfur substitutions were subjected to nuclease resistance assays. FIG. 2 shows an image from the nuclease resistance assay for sDNA with DNase I. 0.25 nmol of: A) AT15; B) As10Ts10; C) As10Ts20; and D) As20Ts20 were incubated for 0 to 12 hours and run on a 7% native polyacrylamide gel. The gel was stained with ethidium bromide and visualized using an AlphaImager.

The sDNA stability and nuclease activity was confirmed prior to experiments by polyacrylamide gel electrophoresis of the sDNA and enzymatic assays confirming the activity of the nuclease. No DNA was detected after 30 minutes incubation when DNA with no sulfur substitutions or with sulfur substitutions in alternate nucleotide positions was used (FIG. 2, lanes A and B). The majority of DNA containing one strand with alternating sulfur substitution and the other strand with contiguous sulfur substitution was digested after 6 hours (FIG. 2, lane C). Only DNA with complete and contiguous sulfur substitutions on both strands remained undigested after 12 hours of incubation with DNaseI (FIG. 2, lane D).

EXAMPLE 3

HMGA1 Expression Levels in Pancreatic Cancer Cell Lines

HMGA1 expression in three human pancreatic cancer cell lines, AsPC-1, Miapaca-2 and Panc-1, was examined by Western blot analysis. The results of a western blot analysis of A) HMGA1 and B) HMGA2 expression levels in pancreatic cancer cell lines are shown on FIGS. 3A-B and 4A-B, respectively. In the assays shown in FIGS. 3A-B and 4A-B, nuclear extracts of AsPC-1, Miapaca-2, and Panc-1 cell lines were run on a 4-12% gradient gel. In each lane, 25 µg of total nuclear protein was loaded.

Figure 5A:
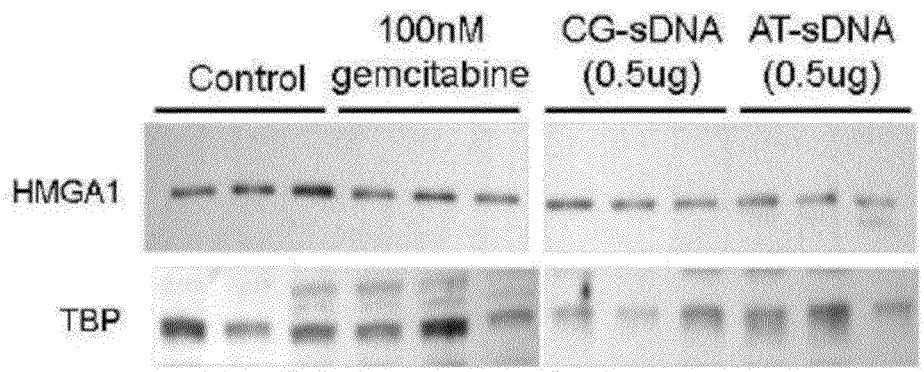
FIG. 5A contains images and a FIG. 5B is a corresponding graph showing the results of an assay in which 15 μg of total nuclear protein was loaded in each lane after AsPC-1 cells treated with 100 nM gemcitabine for 48 hours and transfected with 0.5 μg of CG-sDNA, or AT-sDNA in six well plates for 48 hours. The control is nuclear extract from untreated cells.
Figure 5B:
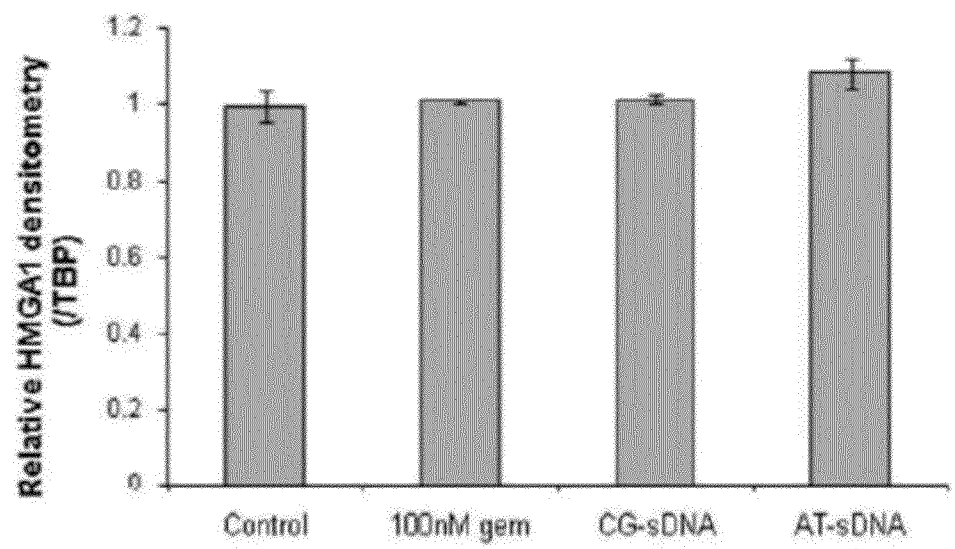

FIGS. 5A-B reflects the results of the western blot analysis measuring HMGA1 expression levels after transfection with CG-sDNA or AT-sDNA and in the presence of gemcitabine. 15 µg of total nuclear protein was loaded in each lane after AsPC-1 cells treated with 100 nM gemcitabine for 48 hours and transfected with 0.5 µg of CG-sDNA, or AT-sDNA in six well plates for 48 hours. The control was nuclear extract from untreated cells.

Triplicates of each sample were run on the gel and analyzed with the Alpha Imager. The relative HMGA1 densities were obtained by dividing HMGA density by TBP density. The values were analyzed pair wise using a student t-test, with p values <0.05 considered a significant change (*p<0.05). TATA binding protein (TBP) was used as a loading control.

Figure 3A:
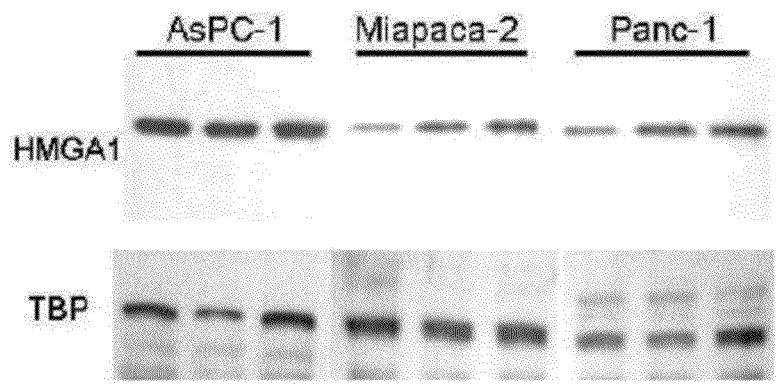
FIGS. 3A and 4A are images and FIGS. 3B and 4B are corresponding graphs showing the results of a western blot analysis of HMGA1 (FIGS. 3A and 3B) and HMGA2 (FIGS. 4A and 4B) expression levels in pancreatic cancer cell lines. Nuclear extracts of AsPC-1, Miapaca-2, and Panc-1 cell lines were run on a 4-12% gradient gel. In each lane, 25 μg of total nuclear protein was loaded.
Figure 3B:
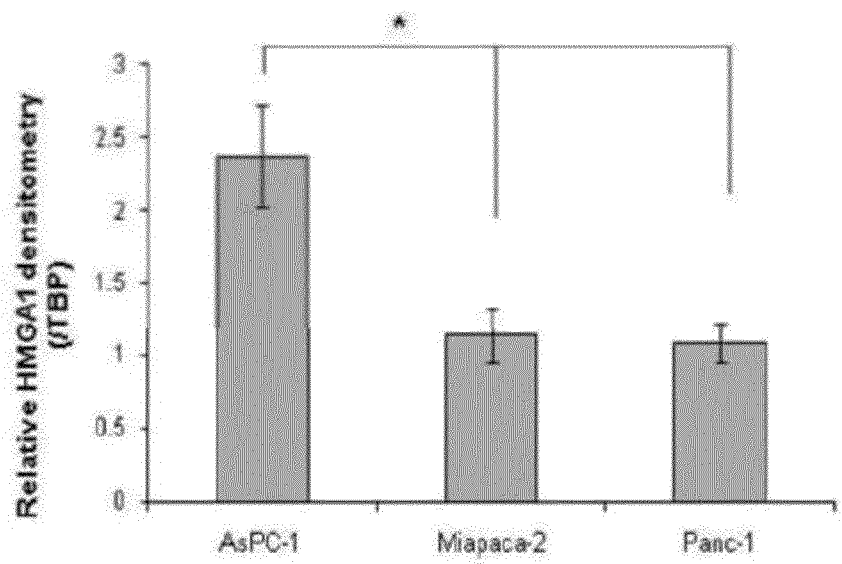
Figure 4A:
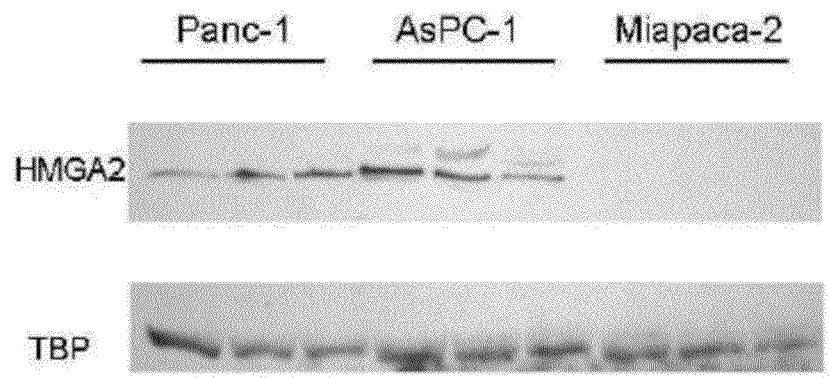
Figure 4B:
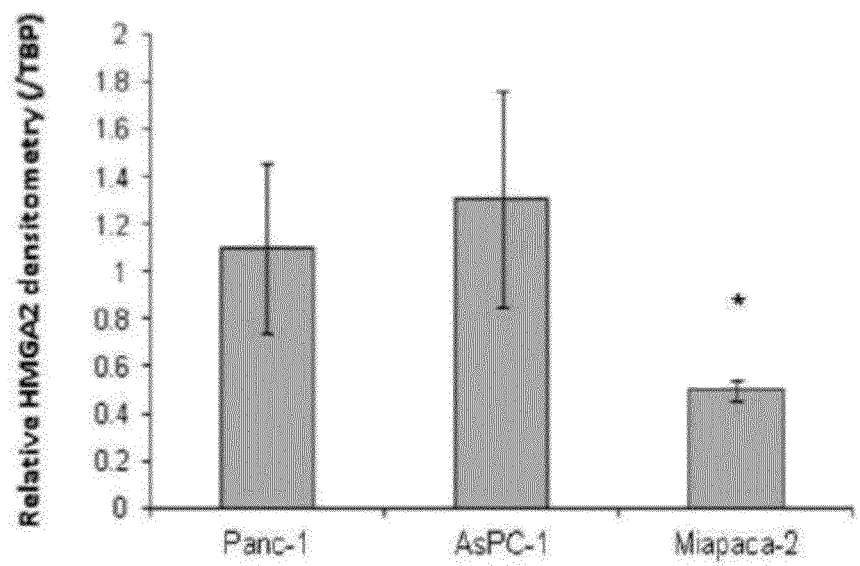

AsPC-1 had the highest HMGA1 expression compared to Miapaca-2 and Panc-1 (FIGS. 3A-B). The expression levels of HMGA2 are shown in FIG. 4A-B. While AsPC-1 express both HMGA1 and HMGA2, no HMGA2 protein expression was detected in Miapaca-2 cells. AsPC-1 cells treated with 100 nM gemcitabine exhibited no change in HMGA1 expression levels (FIGS. 5A-B).

This experiment was conducted to ensure that transfection of the aptamer or gemcitabine into the cancer cells would not change the HMGA1 protein expression levels in the cells. HMGA1 expression levels were examined after transfection with CG-sDNA or AT-sDNA to determine if the transfection procedure affected HMGA1 expression levels. The AT-sDNA used for transfection contained an 18 adenine/thymine stretch enabling HMGA1 to bind the DNA with all three AT-hooks. As a negative control, a non-HMGA1-targeted sDNA containing an equal length of DNA but with no AT-stretches, i.e. CG-sDNA, was used. Western blot analyses indicated no changes in HMGA1 expression levels after AT-sDNA or CGsDNA transfection (FIGS. 5A-B). We also tested transfection of the cells with 100 nM gemcitabine and observed no change in HMGA expression levels.

EXAMPLE 4

Effect of sDNA on Cell Growth

The dependence of Miapaca-2 and AsPC-1 cell viability on transfection with Mix-sDNA, CG-sDNA and AT-sDNA was assessed after 48 and 96 hours. The results of this assay are shown on FIGS. 6A and 6B and reported on Table 1 below. After sDNA transfection with two doses of sDNA, Miapaca-2 (FIG. 6A) and AsPC-1 (FIG. 6B) cells were fixed 48 and 96 hours and analyzed with the crystal violet assay as described in the Material and Methods section above. The absorbance was measured at 570 nm in quadruplicate. All data from control cells were combined and averaged. The values were analyzed pair wise with transfection control (TC) cells using a student t-test, with p values <0.05 considered a significant change (*$p<0.05$, **$p<0.01$).

The effect of transfection alone on cell viability was assessed to establish a transfection control (TC) baseline for comparison with combinations of sDNA transfections and gemcitabine treatment. The TC cells were transfected with Lipofectamine 200 carrying only a vehicle and cell growth was compared to the untransfected (UT) control cells (FIGS. 6A, 6B).

In Miapaca-2, TC cells showed a 37.7% ($p<0.005$) and 37.6% ($p<0.01$) decrease in cell growth compared to UT cells after 48 and 96 hours, respectively (FIG. 6A), whereas in AsPC-1, TC cells showed 25.3% ($p<0.005$) and 7.9% ($p>0.05$) decrease in cell growth after 48 and 96 hours, respectively, compared to UT cells (FIG. 6B). Similar decreases in cell growth were observed after 0.1 ug of transfection with two sDNA controls, Mix-sDNA and CG-sDNA (FIGS. 6A, 6B). Specifically, in AsPC-1 cells, 28.0% ($p<0.005$) and 33.8% ($p<0.0005$) of cells were dead with Mix-sDNA and CG-sDNA transfection after 48 hrs, and 19.4% ($p<0.01$) and 14.3% ($p<0.05$) of cells were dead after 96 hrs, respectively. In Miapaca-2, 30.4% ($p<0.001$) and 36.3% ($p<0.005$) of cells were dead with Mix-sDNA and CG-sDNA transfection after 48 hrs, and 33.3% ($p<0.01$) and 32.0% ($p<0.001$) of cells were dead after 96 hrs, respectively. (FIGS. 6A, 6B)

These results showed that both transfection with non-AT rich sDNA and TC cells had significantly decreased cell viability compared to UT control cells. However, comparisons between TC cells and cells transfected with Mix-sDNA, and CG-sDNA showed no significant differences between these treatments ($p>0.05$) at both 48 and 96 hours. (FIGS. 6A, 6B)

When cells were transfected with AT-sDNA, however, significant decreases in cell viability were observed compared to UT and TC controls. In Miapaca-2, 48.4% ($p<0.005$) and 17.2% ($p<0.05$) of the cells were dead after 48 hrs compared to UT and TC controls, respectively, and after 96 hrs, 58.9% ($p<0.001$) and 34.1% ($p<0.01$) of cells were dead, respectively. In AsPC-1 cells, 42.0% ($p<0.005$) and 22.3% ($p<0.05$) of cells were dead compared to UT and TC controls after 48 hrs, and 36.1% ($p<0.001$) and 30.7% ($p<0.01$) of cells were dead after 96 hrs, respectively.

The effect of sDNA transfection dose was also examined using AsPC-1 cells. Cells were transfected with four different CG-sDNA and AT-sDNA doses, 0.025, 0.1, 0.25 and 1 μg, and cell growth compared to TC cells at 48 (FIG. 7A) and 96 hours (FIG. 7B). When cells were transfected with 1.0 μg of sDNA, more than half of the cells were dead after 96 hours for both AT-sDNA (53.6%, $p<0.0005$) and CG-sDNA (56.4%, $p<0.001$). This result showed that 1.0 of sDNA transfection was highly toxic to the cells independent of DNA sequence. Therefore, lower dosages of sDNA were used to characterize sensitivity to DNA transfection. When 0.25 μg sDNA was used for transfection, both cells lines were more viable compared to the 1.0 μg sDNA transfected cells, however, cell death was greater in cells transfected with AT-sDNA (39.4%, $p<0.01$) compared to CG-sDNA (9.0%, $p<0.05$).

As the amount of sDNA transfected was decreased to 0.1 μg, the cell death rates for the two cell lines transfected with CG-sDNA and AT-sDNA were similar to 0.25 μg transfection; 9.7% ($p<0.05$) CG-sDNA, and 30.7% ($p<0.01$) AT-sDNA. FIGS. 7A, 7B. Transfection with 0.025 μg of sDNA had very little affect on cell growth, with only an 8.5% ($p<0.05$) decrease in viability observed for AT-sDNA transfected cells whereas the reduction in CG-sDNA transfected cells was not statistically significant compared to TC cells ($p>0.05$). The 0.25 μg and 0.1 μg sDNA treatments, however, showed statistically significant differences between AT-sDNA and CG-sDNA transfected cells with $p=0.007$ and $p=0.047$, respectively. FIGS. 7A, 7B.

These results indicated that inhibition of HMGA1 activity caused increased cell death or apoptosis even in the absence of chemotherapy treatment.

EXAMPLE 5

Gemcitabine Treatment and Cell Growth in the Presence of sDNA Aptamers

Cells transfected with 0.1 or 0.25 μg of sDNA were treated with six different concentrations of gemcitabine: 0, 1, 10, 30, 100, 1000 nM. Cells were fixed after 96 hours and numbers of viable cells counted by measuring the absorbance at 570 nm. $IC_{50}$ values calculated based upon the concentration of either gemcitabine or sDNA at which only half the cell growth is observed compared to the control experiment in absence of gemcitabine or sDNA. FIGS. 8A-D and Table 1 report the $IC_{50}$ determinations for the various doses of sDNA transfection with gemcitabine treatment: 0.1 μg transfection for AsPC-1 (FIG. 8A); 0.25 μg transfection for AsPC-1 (FIG. 8B); 0.1 μg transfection for Miapaca-2 (FIG. 8C); and, 0.25 μg transfection for Miapaca-2 (FIG. 8D).

TABLE 1

Fold changes in numbers of viable cells between UT and transfected cells 96 h after transfection. Fold changes in numbers of viable cells between TC and sDNA transfected cells 96 h after transfection are indicated in the parentheses.

|  | UT | TC | Mix | CG | AT |
|---|---|---|---|---|---|
| Miapaca-2 (0.1 μg) | 1.00 | −1.55 (1.00) | −1.45 (1.07) | −1.43 (1.09) | −2.36 (−1.52) |
| Miapaca-2 (0.25 μg) | 1.00 | −1.65 (1.00) |  | −2.15 (−1.30) | −6.07 (−3.68) |

TABLE 1-continued

Fold changes in numbers of viable cells between UT and transfected cells 96 h after transfection. Fold changes in numbers of viable cells between TC and sDNA transfected cells 96 h after transfection are indicated in the parentheses.

|  | UT | TC | Mix | CG | AT |
|---|---|---|---|---|---|
| AsPC-1 (0.1 μg) | 1.00 | −1.09 (1.00) | −1.24 (−1.14) | −1.20 (−1.11) | −1.57 (−1.44) |
| AsPC-1 (0.25 μg) | 1.00 | −1.09 (1.00) |  | −1.19 (−1.10) | −1.79 (−1.65) |

Significant decreases in gemcitabine $IC_{50}$ values were observed in AsPC-1 cells with AT-sDNA treatment (FIGS. 8A and 8B, Table 2). For example, at 0.1 and 0.25 μg AT-sDNA treatments, $IC_{50}$ values were 3.8+0.2 nM and 1.8+0.13 nM, respectively compared to TC values of 27.98+1.4 nM and 24.8+1.45 nM, respectively.

TABLE 2

Gemcitabine $IC_{50}$ values of AsPC-1 and Miapaca-2 cells after 0.025, 0.1 and 0.25 μg sDNA transfections.

| Cell line | Transfection | $IC_{50}$ values (nM) | | |
|---|---|---|---|---|
|  |  | 0.025 μg | 0.1 μg | 0.25 μg |
| AsPC-1 | TC |  | 27.98 ± 1.4 | 24.8 ± 1.45 |
|  | Mix-sDNA |  | 69.4 ± 1.1 |  |
|  | CG-sDNA | 171.53 ± 26.6 | 24.2 ± 2.2 | 46.5 ± 1.6 |
|  | AT-sDNA | 107.49 ± 39.6 | 3.8 ± 0.2 | 1.8 ± .13 |
| Miapaca-2 | TC |  | 11.91 ± 1.2 | 21.5 ± 0.6 |
|  | Mix-sDNA |  | 20.43 ± 1.25 |  |
|  | CG-sDNA |  | 15.11 ± 1.30 | 21.4 ± 1.3 |
|  | AT-sDNA |  | 13.63 ± 1.52 | 21.6 ± 1.3 |

The $IC_{50}$ values for the AT-sDNA treatments were also substantially smaller compared to the two control sDNA transfections with the Mix-sDNA having values of 69.4+1.1 nM for 0.1 μg, and the CG-sDNA having values of 24.2+2.2 nM and 46.5+1.6 nM, respectively. (See Table 2) These results indicated that AspC-1 cells transfected with AT-sDNA were more sensitive to gemcitabine chemotherapy treatment compared to cells that did not receive this treatment.

On the other hand, no significant changes in $IC_{50}$ values were found in Miapaca-2 cells (FIGS. 8C and 8D). However, there was a significant overall drop (~10-fold, Table 3) in the number of viable Miapaca-2 cells after either 0.1 or 0.25 μg AT-sDNA transfection at doses of 100 nm or greater gemcitabine. While the AsPC-1 cells experienced a significant drop in gemcitabine $IC_{50}$, the overall drop in the number of viable cells after gemcitabine treatment was considerably smaller (2-4 fold) compared to that observed for Miapaca-2 cells (Table 3).

These results indicated that cell death due to AT-sDNA transfection was substantially greater in Miapaca-2 cells compared to AsPC-1 cells. The increased cell death due to AT-sDNA transfection in comparison to controls (Table 1) presumably was a result of inhibition of HMGA proteins. The greater sensitivity of Miapaca-2 cells to AT-sDNA compared to AsPC-1 cells probably has to do with the fact that Miapaca-2 cells only express HMGA1 whereas AsPC-1 cells express both HMGA1 and HMGA2. Therefore, the effective dose of AT-sDNA towards HMGA proteins is higher to Miapaca-2 cells in comparison to AsPC-1 cells. Neither cell line treated with gemcitabine for 48 hours showed a dose dependent response (FIG. 9A-B). This was probably due to the fact that the cell doubling times of both Miapaca-2 and AsPC-1 cells are longer than 48 hours.

After 96 hours of gemcitabine treatment, Miapaca-2 cells showed increased dose dependent responses at 0.1 μg AT-sDNA transfection compared to AsPC-1 cells at either 0.1 μg or 0.25 μg AT-sDNA transfections (FIGS. 10A-D, 11A-D, 12A-C; Table 3). FIGS. 10A-D reports a dose dependent response to gemcitabine treatment after sDNA transfection in Miapaca-2 at 96 hours. Cells were transfected with 0.1 μg of TC-sDNA, Mix-sDNA, CG-sDNA, and AT-sDNA. FIGS. 11A-D and 12A-C report dose dependent responses to gemcitabine treatment in AsPC-1 at 96 hours and 0.1 μg (FIGS. 11A-D), and 0.25 μg (FIGS. 12A-C) transfection. The data was normalized with the 0 nM gemcitabine treated cells and the resulting value defined as a value of 1. The values were analyzed in pairs using a student t-test, with p values <0.05 considered a significant change (*p<0.05, p<0.01, *p<0.001).

Responses to various concentrations of gemcitabine were similar among the three controls, TC, Mix and CG. (FIGS. 7A-B) A significant increase in sensitivity to 10 nM gemcitabine was observed in Miapaca-2 cells transfected with AT-sDNA with only 51.2% (p<0.05) of cells surviving compared to 77.1% (p<0.05) in TC, 94.5% (p>0.05) in Mix-sDNA, and 83.9% (p>0.05) in CG-sDNA. In addition, at 1 nM gemcitabine treatment, 33.6% (p<0.05), cells were dead with AT-sDNA transfection whereas no significant change in cell viabilities were observed in TC, Mix-sDNA, and CG-sDNA transfected cells. At higher gemcitabine treatments, 30, 100 and 1000 nM, significant decreases in cell viabilities were found in all the transfected cells (9.6-35.2%, p<0.001) after 96 hours.

AsPC-1 cell sensitivity to gemcitabine treatment was assayed for 0.1 and 0.25 μg sDNA transfection doses at six different gemcitabine concentrations (FIGS. 9A-B; Table 3). Within the AT-sDNA transfection set of experiments, the dose dependent responses to gemcitabine were stronger at the 0.25 μg transfection compared to the 0.1 μg transfection. For example, 14.9% (p<0.05) and 41.7% (p<0.05) of the cells died in the 0.25 μg AT-sDNA transfections at 1 and 100 nM gemcitabine doses, respectively, compared to 9.0% (p>0.05) and 29.4% (p<0.05) of cells dying at 1 and 100 nM gemcitabine treatments with 0.1 μg AT-sDNA transfection, respectively. At the lowest AT-sDNA transfection dose of 0.025 μg, an insignificant effect on cell viability was observed with only 8.5% cell death (p>0.05) in the absence gemcitabine treatment (FIG. 6B), whereas cell death increased significantly to 31% (p<0.05) when 1000 nM gemcitabine treatment was administered (FIGS. 10A-D, 11A-D, 12A-C).

TABLE 3

Fold changes in numbers of viable cells normalized relative to TC for various sDNA transfections as a function of gemcitabine treatment.

| sDNA used for transfection | | Gemcitabine (nM) | | | | | |
|---|---|---|---|---|---|---|---|
| | | 0 | 1 | 10 | 30 | 100 | 1000 |
| Miapaca-2 (0.1 ug) | TC | 1.00 | 1.00 | −1.30 | −3.21 | −3.59 | −3.47 |
| | Mix | 1.07 | 1.12 | 1.01 | −2.65 | −4.41 | −4.48 |
| | CG | 1.09 | 1.12 | −1.09 | −3.29 | −4.06 | −4.24 |
| | AT | −1.52 | −1.38 | −1.79 | −7.07 | −9.58 | −6.82 |
| Miapaca-2 (0.25 ug) | TC | 1.00 | 1.00 | −1.30 | −3.21 | −3.59 | −3.47 |
| | CG | −1.30 | −1.38 | −1.37 | −2.97 | −5.48 | −4.11 |
| | AT | −3.68 | −4.45 | −4.14 | −8.32 | −11.81 | −11.31 |
| AsPC-1 (0.1 ug) | TC | 1.00 | 1.14 | −1.02 | −1.04 | −1.36 | −1.52 |
| | Mix | −1.14 | −1.06 | −1.16 | −1.17 | −1.36 | −1.59 |
| | CG | −1.11 | −1.09 | −1.18 | −1.34 | −1.52 | −1.67 |
| | AT | −1.44 | −1.58 | −1.71 | −1.86 | −2.04 | −2.33 |
| AsPC-1 (0.25 ug) | TC | 1.00 | 1.14 | −1.02 | −1.04 | −1.36 | −1.52 |
| | CG | −1.10 | −1.10 | −1.21 | −1.69 | −1.36 | −2.16 |

In light of the foregoing, it should be appreciated that the present invention significantly advances the art by providing an HGMA-targeted phosphorothioate DNA aptamers for use in suppressing carcinogenic activity and increasing sensitivity to chemotherapy agents in human cancer cells that are structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

SEQUENCE LISTING

```
<160> NUMBER OF SEQ ID NOS: 13

<210> SEQ ID NO 1
<211> LENGTH: 24
<212> TYPE: DNA
<213> ORGANISM: Artificial sequence
<220> FEATURE:
<223> OTHER INFORMATION: Synthetic oligodeoxynucleotide with
      phosphorothioate internucleotide linkages

<400> SEQUENCE: 1
gggaaaaaat tttttaaaaa accc                                           24

<210> SEQ ID NO 2
<211> LENGTH: 21
<212> TYPE: DNA
<213> ORGANISM: Artificial sequence
<220> FEATURE:
<223> OTHER INFORMATION: Synthetic oligodeoxynucleotide with
      phosphorothioate internucleotide linkages

<400> SEQUENCE: 2
cccaaaaaaa aaaaaaaacc c                                              21

<210> SEQ ID NO 3
<211> LENGTH: 21
<212> TYPE: DNA
<213> ORGANISM: Artificial sequence
<220> FEATURE:
<223> OTHER INFORMATION: Synthetic oligodeoxynucleotide with
      phosphorothioate internucleotide linkages

<400> SEQUENCE: 3 gggtttttttt ttttttttgg g                                             21

<210> SEQ ID NO 4
<211> LENGTH: 29
```

```
<212> TYPE: DNA
<213> ORGANISM: Artificial sequence
<220> FEATURE:
<223> OTHER INFORMATION: Synthetic oligodeoxynucleotide

<400> SEQUENCE: 4
cgcggggccg ccgcgaaaaa aaaaaaccc                                    29

<210> SEQ ID NO 5
<211> LENGTH: 28
<212> TYPE: DNA
<213> ORGANISM: Artificial sequence
<220> FEATURE:
<223> OTHER INFORMATION: Synthetic oligodeoxynucleotide with
      phosphorothioate internucleotide linkages from base pair 4 to base
      pair 14

<400> SEQUENCE: 5
gggttttttt tttcgcggcg gccccgcg                                     28

<210> SEQ ID NO 6
<211> LENGTH: 28
<212> TYPE: DNA
<213> ORGANISM: Artificial sequence
<220> FEATURE:
<223> OTHER INFORMATION: Synthetic oligodeoxynucleotide

<400> SEQUENCE: 6
gggccccccc ccccgcggcg gccccgcg                                     28

<210> SEQ ID NO 7
<211> LENGTH: 28
<212> TYPE: DNA
<213> ORGANISM: Artificial sequence
<220> FEATURE:
<223> OTHER INFORMATION: Synthetic oligodeoxynucleotide

<400> SEQUENCE: 7
gggcgtgact gagcgcggcg gccccgcg                                     28

<210> SEQ ID NO 8
<211> LENGTH: 21
<212> TYPE: DNA
<213> ORGANISM: Artificial sequence
<220> FEATURE:
<223> OTHER INFORMATION: Synthetic oligodeoxynucleotide

<400> SEQUENCE: 8
cccaaaaaaa aaaaaaaacc c                                            21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligodeoxynucleotide

<400> SEQUENCE: 9
gggttttttt tttttttttgg g                                           21

<210> SEQ ID NO 10
<211> LENGTH: 21
<212> TYPE: DNA
<213> ORGANISM: Artificial sequence
<220> FEATURE:
<223> OTHER INFORMATION: Synthetic oligodeoxynucleotide with
      phosphorothioate internucleotide linkages from base pairs 2 to 3,
```

-continued

```
       4 to 5, 6 to 7, 8 to 9, 10 to 11, 12 to 13, 14 to 15, 16 to 17, 18
       to 19, and 20 to 21.

<400> SEQUENCE: 10
cccaaaaaaa aaaaaaaacc c                                                 21

<210> SEQ ID NO 11
<211> LENGTH: 21
<212> TYPE: DNA
<213> ORGANISM: Artificial sequence
<220> FEATURE:
<223> OTHER INFORMATION: Synthetic oligodeoxynucleotide with
      phosphorothioate internucleotide linkages from base pairs 1 to 2,
      3 to 4, 5 to 6, 7 to 8, 9 to 10, 11 to 12, 13 to 14, 15 to 16, 17
      to 18, and 19 to 20.

<400> SEQUENCE: 11 gggtttttttt tttttttttgg g                                               21

<210> SEQ ID NO 12
<211> LENGTH: 24
<212> TYPE: DNA
<213> ORGANISM: Artificial sequence
<220> FEATURE:
<223> OTHER INFORMATION: Synthetic oligodeoxynucleotide with
      phosphorothioate internucleotide linkages

<400> SEQUENCE: 12
ccccgggccc cggccgggcg ccgc                                              24

<210> SEQ ID NO 13
<211> LENGTH: 24
<212> TYPE: DNA
<213> ORGANISM: Artificial sequence
<220> FEATURE:
<223> OTHER INFORMATION: Synthetic oligodeoxynucleotide with
      phosphorothioate internucleotide linkages

<400> SEQUENCE: 13
cccactgcag tcggactcac tcgc                                              24
```

What is claimed is:

1. An sDNA aptamer for suppressing the carcinogenic activity of High Mobility Group A (HMGA) proteins in human cells having a nucleotide sequence comprising a segment selected from the group consisting of: 5'-G*G*G*A*A*A*A*A*A*T*T*T*T*T*T*A*A*A*A* A*A*-C*C*C-3' (SEQ ID NO: 1); 5'-C*C*C*A*A*A*A*A*A* A*A*A*A*A*A*A*A*C*C*C-3' (SEQ ID NO: 2); 5'-G*G*G*T*T*T*T*T*T*T*T*T*T*T*T*T*T*T*G*G* G-3' (SEQ ID NO: 3); 5'-GGGT*T*T*T*T*T*T* T*T*T*CGCGGCGGCCCCGCG-3' (SEQ ID NO: 5); 5'-CC*CA*AA*AA*AA*AA*AA*AA*AA*CC*C-5' (SEQ ID NO: 10), and 5'-G*GG*TT*TT*TT*TT*TT*TT*TT*TG*GG-3' (SEQ ID NO: 11); wherein are phosphorothioate linkages.

2. The sDNA aptamer of claim 1 wherein the length of the sDNA aptamer is from about 17 to about 30 base pairs.

3. The sDNA aptamer of claim 1 having the sequence 5'-G*G*G*A*A*A*A*A*A*A*T*T*T*T*T*T*A*A*A*A* A*A*C*C*C-3' (SEQ ID NO.: 1) wherein the * are phosphorothioate linkages.

4. The sDNA aptamer of claim 1 wherein said sDNA aptamer can be transfected into at least one human cell type.

5. The sDNA aptamer of claim 1 wherein said sDNA aptamer inhibits HMGA protein activity in human cancer cells by providing binding sites for said HGMA proteins, thereby preventing them from binding to genomic DNA.

6. The sDNA aptamer of claim 5 wherein said human cancer cells are human pancreatic adenocarcinoma cells.

7. The sDNA aptamer of claim 6 wherein said sDNA aptamer increases sensitivity of human cancer cells to gemcitabine.

8. The sDNA aptamer of claim 7 wherein said human cancer cells are human pancreatic adenocarcinoma cells.

9. The sDNA aptamer of claim 1 wherein said sDNA aptamer is contained within a nanoparticle-aptamer bioconjugate for delivery to cells in vivo.

* * * * *